(12) United States Patent
Towell et al.

(10) Patent No.: US 9,579,397 B1
(45) Date of Patent: Feb. 28, 2017

(54) COMPUTER-IMPLEMENTED SYSTEMS AND METHODS FOR ANALYZING COURT ACTIVITY

(75) Inventors: Dwayne E. Towell, Abilene, TX (US); Darryl E. Towell, Abilene, TX (US); Amy George Towell, Abilene, TX (US)

(73) Assignee: Hopkins Bruce Research Corporation, Abilene, TX (US)

( * ) Notice: Subject to any disclaimer, the term of this patent is extended or adjusted under 35 U.S.C. 154(b) by 440 days.

(21) Appl. No.: 12/773,366

(22) Filed: May 4, 2010

Related U.S. Application Data

(60) Provisional application No. 61/175,689, filed on May 5, 2009, provisional application No. 61/225,089, filed on Jul. 13, 2009.

(51) Int. Cl.
*G06F 17/30* (2006.01)
*A61K 48/00* (2006.01)

(52) U.S. Cl.
CPC .................................. *A61K 48/00* (2013.01)

(58) Field of Classification Search
USPC ................................................ 707/740, 802
See application file for complete search history.

(56) References Cited

U.S. PATENT DOCUMENTS

| | | | |
|---|---|---|---|
| 6,926,280 B2 * | 8/2005 | Abuan | A63F 3/00157 273/274 |
| 7,139,734 B2 * | 11/2006 | Nathans | G06Q 20/00 705/38 |
| 7,877,322 B2 * | 1/2011 | Nathans | G06Q 20/00 705/38 |
| 7,983,990 B2 * | 7/2011 | Bennett | G06F 17/30637 705/59 |
| 8,055,529 B1 * | 11/2011 | Jackson | G06Q 10/0639 705/7.29 |
| 2004/0178581 A1 * | 9/2004 | Abuan | A63F 3/00157 273/292 |
| 2008/0027859 A1 * | 1/2008 | Nathans | G06Q 10/00 705/38 |
| 2008/0195604 A1 * | 8/2008 | Sears | G06F 17/30728 |
| 2009/0222717 A1 * | 9/2009 | Nelson | G06F 17/30887 715/207 |

(Continued)

OTHER PUBLICATIONS

LexisNexis website, http://www.lexisnexis.com/.

(Continued)

*Primary Examiner* — Kim Nguyen
(74) *Attorney, Agent, or Firm* — Michael Best & Friedrich LLP

(57) ABSTRACT

A method of analysis and presentation of court document information includes: at least one of one or more servers providing, to a user, a user interface, the user interface permitting assignment, for each court ruling associated with a court document stored in a searchable database, of one or more of pre-defined categories relating to the ruling, the one or more pre-defined categories including at least one of: (a) a type of procedural vehicle that led to the ruling; (b) a description of the procedural vehicle that led to the ruling; and (c) the court's ruling; and at least one of the one or more servers arranging the categorized court rulings in the searchable database, such that the court documents can be searched on the basis of at least one or more of the assigned pre-defined categories.

30 Claims, 32 Drawing Sheets

(56) References Cited

U.S. PATENT DOCUMENTS

2010/0100572 A1* 4/2010 Schiller .................. G06Q 10/10
707/805

OTHER PUBLICATIONS

Westlaw website, http://web2.westlaw.com.
LexMachina website, http://lexmachina.com/.
RFC Express website, http://www.rfcexpress.com/.
Justia website, http://www.justia.com/.
Findlaw website, http://www.findlaw.com/.
Loislaw website, http://www.loislaw.com/.
TheLaw.Net website, http://www.thelaw.net/.
Bloomberg Law website, https://www.bloomberglaw.com/login.htm.
Legal Metric website, http://www.legalmetric.com/.
Innography website, http://www.innography.com/.
MaxVal website, http://www.maxval-ip.com/.
RECAP website, https://www.recapthelaw.org/.
Courthouse News Service website, http://www.courthousenews.com/.
PACER website, http://www.pacer.gov/.
Case Law website, http://www.case-law.us/.
Court Web website, http://courtweb.pamd.uscourts.gov/courtweb/courtweb.aspx.
PriorSMart website, http://news.priorsmart.com/.

\* cited by examiner

ID: 57389     CACD WESTERN DIVISION 2-07-CV-06222

RONALD A. KATZ TECHNOLOGY LICENSING L P V. ECHOSTAR COMMUNICATIONS CORPOR

DOCKET NUM: 441     FILED 4/30/2009     WEB CASE   WEB .PDF   LOCAL .PDF   LOCAL .XLS

DISCOVERY SPECIAL MASTER'S ORDER GRANTING JOINT STIPULATION REGARDING COLLECTIVE AGREEMENT
FOR EXCHANGE OF EXPERT COMPENSATION INFORMATION FILED BY PLAINTIFF RONALD A. KATZ TECHNOLOGY LICENSING L
P (POCHE THOMAS) (ENTERED 04/30/2009)

KTOW

TOTAL: [DONE ▸]
PATENTS: [ ▸]
REMEDIES: [ ▸]
FILERS: [DONE ▸]
EVENTS: [DONE ▸]
DECL'TIONS: [ ▸]
TERMS: [ ▸]
ANNO'TIONS: [ ▸]

| CASE JUDGES | CASE PARTIES/PATENTS | FILERS | EVENTS | REMEDIES | DECLARATIONS | CLAIM TERMS |
|---|---|---|---|---|---|---|

| CAUSE | ACTION | RESULT |
|---|---|---|
| ⊞ STIPULATION/AGREED/UNOPPOSE | MOT FOR PROTECT ORDER -- PRESERVE CONFIDENT | GRANTED |
| ⊞ STIPULATION/AGREED/UNOPPOSE | MOT TO COMPEL DISCOVERY ▸ | GRANTED |
| * | | |

FIG. 4

| | A | B | C | D | E | F | G | H | I |
|---|---|---|---|---|---|---|---|---|---|
| 129 | 4/13/2009 | 124 | RESPONSE TO 117 MOTION FOR PARTIAL SUMMARY JUDGMENT EXCLUDING CERTAIN PRIOR ART, FILED BY MAERSK CONTRACTORS USA INC., (ATTACHMENTS: #1 APPENDIX, #2 EXHIBIT 1, #3 EXHIBIT 2, #4 EXHIBIT 3, #5 EXHIBIT 4, #6 EXHIBIT 5, #7 EXHIBIT 6, #8 EXHIBIT 7, #9 ERRATA 8, #10 EXHIBIT 9, #11 EXHIBIT 10, #12 EXHIBIT 11, #13 EXHIBIT 12, #14 EXHIBIT 13, #15 EXHIBIT 14, #16 EXHIBIT 15, #17 EXHIBIT 16, #18 EXHIBIT 17, #19 EXHIBIT 18, #20 PROPOSED ORDER)(KAPLAN, LEE) (ENTERED: 04/13/2009) | | | | | | |
| 130 | 4/13/2009 | 125 | SEALED EVENT, FILED, (WITH ATTACHMENTS) (ENTERED: 04/13/2009) | | | | | | |
| 131 | 4/14/2009 | 126 | ORDER - A HEARING ON VARIOUS/SELECTED MOTIONS IS SET FOR 4/30/2009 AT 9:00 AM IN COURTROOM 11A BEFORE JUDGE KENNETH M. HOYT. (SIGNED BY JUDGE KENNETH M. HOYT) PARTIES NOTIFIED. (DPALACIOS) (ENTERED: 04/14/2009) | | | | | | |
| 132 | 4/14/2009 | 127 | RESPONSE TO 113 MOTION FOR SUMMARY JUDGMENT FOR NON INFRINGEMENT, FILED BY TRANSOCEAN OFFSHORE DEEPWATER DRILLING, INC. (ATTACHMENTS: #1 PROPOSED ORDER, #2 EXHIBIT 1, #3 EXHIBIT 2, #4 EXHIBIT 3, #5 EXHIBIT 5 PART 1, #6 EXHIBIT 5 PART 2, #7 EXHIBIT 7) (WALKER, CHARLES) (ENTERED: 04/14/2009) | | | | | | |
| 133 | 4/14/2009 | 128 | SEALED EVENT, FILED (WITH ATTACHMENTS) (ENTERED: 04/14/2009) | | | | | | |
| 134 | 4/15/2009 | 129 | MOTION TO SEAL TRANSOCEAN'S RESPONSE TO MAERSK'S MOTION FOR SUMMARY JUDGMENT FOR NON-INFRINGEMENT BY TRANSOCEAN OFFSHORE DEEPWATER DRILLING, INC., FILED MOTION DOCKET DATE 5/5/2009 (ATTACHMENTS: #1 PROPOSED ORDER) (WALKER, CHARLES) (ENTERED: 04/15/2009) | | | | | | |
| 135 | 4/21/2009 | 130 | REPLY IN SUPPORT OF 113 MOTION FOR SUMMARY JUDGMENT FOR NON INFRINGEMENT, FILED BY MAERSK CONTRACTORS USA INC. (KAPLAN, LEE) (ENTERED: 04/21/2009) | | | | | | |
| 136 | 4/21/2009 | 131 | REPLY TO RESPONSE TO 117 MOTION FOR PARTIAL SUMMARY JUDGMENT EXCLUDING CERTAIN PRIOR ART, FILED BY TRANSOCEAN OFFSHORE DEEPWATER DRILLING, INC. (ATTACHMENTS: #1 EXHIBIT Q) (WALKER, CHARLES) (ENTERED: 04/21/2009) | | | | | | |
| 137 | 4/21/2009 | 132 | SEALED EVENT, FILED, (WITH ATTACHMENTS) (ENTERED: 04/21/2009) | | | | | | |
| 138 | 4/22/2009 | 133 | ORDER GRANTING 129 MOTION TO SEAL 127 TRANSOCEAN'S RESPONSE TO MAERSK'S MOTION FOR SUMMARY JUDGMENT FOR NON INFRINGEMENT. (SIGNED BY JUDGE KENNETH M. HOYT) PARTIES NOTIFIED (DPALACIOS,) (ENTERED: 04/22/2009) | | | | | | |
| 139 | 4/22/2009 | 134 | ORDER DENYING 110 MOTION FOR LEAVE TO FILE SUR-REPLY REGARDING MAERSK'S MOTION FOR SUMMARY JUDGMENT REGARDING ENABLEMENT. (SIGNED BY JUDGE KENNETH M. HOYT) PARTIES NOTIFIED (DPALACIOS, ) (ENTERED: 04/22/2009) | | | | | | |

FIG. 6

ID: 56284    MND    DMN    0-99-CV-01356

ANCHOR WALL SYSTEMS V. ROCKWOOD RETAINING, ET AL

DOCKET NUM: 829    FILED 3/31/2009    WEB CASE   WEB .PDF LOCAL .PDF LOCAL .XLS

MEMORANDUM OPINION AND ORDER DENYING DEFENDANTS' 656 MOTION FOR JUDGMENT AS A MATTER OF
LAW OR FOR A NEW TRIAL ON THE ISSUE OF INDUCED INFRINGEMENT; DENYING DEFENDANTS' 661 MOTION FOR NEW TRIAL
ON INFRINGEMENT OF THE '713 PATENT; DENYING DEFENDANTS' 664 MOTION FOR JUDGMENT AS A MATTER OF LAW OR FOR

KTOW

TOTAL: ▸ DONE
PATENTS: ▸ DONE
REMEDIES: ▸ DONE
FILERS: ▸ DONE
EVENTS: ▸ DONE
DECL'TIONS: ▸ DONE
TERMS: ▸ DONE
ANNO'TIONS: ▸ DONE

| CASE JUDGES | CASE PARTIES/PATENTS | FILERS | EVENTS | REMEDIES | DECLARATIONS | CLAIM TERMS |

| ROLE | JUDGE NAME |
|---|---|
| ▸ DISTRICT JUDGE | DAVID S. DOTY |
| DISTRICT JUDGE | JOHN R. TUNHEIM |
| MAGISTRATE | FRANKLIN L. NOEL |
| * | |

| ID: 56284 | MND | DMN | 0-99-CV-01356 | | TOTAL: | DONE |
|---|---|---|---|---|---|---|
| ANCHOR WALL SYSTEMS V. ROCKWOOD RETAINING, ET AL | | | | | PATENTS: | |
| DOCKET NUM: 829 | FILED 3/31/2009 | | WEB CASE  WEB .PDF  LOCAL .PDF  LOCAL .XLS | | REMEDIES: | DONE |
| | | | | | FILERS: | DONE |
| MEMORANDUM OPINION AND ORDER DENYING DEFENDANTS' 656 MOTION FOR JUDGMENT AS A MATTER OF LAW OR FOR A NEW TRIAL ON THE ISSUE OF INDUCED INFRINGEMENT; DENYING DEFENDANTS' 661 MOTION FOR NEW TRIAL ON INFRINGEMENT OF THE '713 PATENT; DENYING DEFENDANTS' 664 MOTION FOR JUDGMENT AS A MATTER OF LAW OR FOR | | | | | EVENTS: | DONE |
| | | | | | DECL'TIONS: | DONE |
| | | | | | TERMS: | |
| KTOW | | | | | ANNO'TIONS: | DONE |

| CASE JUDGES | CASE PARTIES/PATENTS | FILERS | EVENTS | REMEDIES | DECLARATIONS | CLAIM TERMS |

PARTY_ID

JUDGE: DISTRICT JUDGE JOHN R. TUNHEIM

*FIG. 8*

| | ID: 56284    MND    DMN    0-99-CV-01356 | TOTAL: | DONE |
|---|---|---|---|
| | ANCHOR WALL SYSTEMS V. ROCKWOOD RETAINING, ET AL | PATENTS: | |
| | DOCKET NUM: 829    FILED 3/31/2009    WEB CASE  WEB .PDF LOCAL .PDF LOCAL .XLS | REMEDIES: | DONE |
| | | FILERS: | DONE |
| | MEMORANDUM OPINION AND ORDER DENYING DEFENDANTS' 656 MOTION FOR JUDGMENT AS A MATTER OF LAW OR FOR A NEW TRIAL ON THE ISSUE OF INDUCED INFRINGEMENT; DENYING DEFENDANTS' 661 MOTION FOR NEW TRIAL ON INFRINGEMENT OF THE '713 PATENT; DENYING DEFENDANTS' 664 MOTION FOR JUDGMENT AS A MATTER OF LAW OR FOR | EVENTS: | DONE |
| | | DECL'TIONS: | DONE |
| | | TERMS: | |
| | KTOW | ANNO'TIONS: | DONE |

CASE JUDGES | CASE PARTIES/PATENTS | FILERS | EVENTS | REMEDIES | DECLARATIONS | CLAIM TERMS

| | CAUSE | ACTION | RESULT |
|---|---|---|---|
| + | MOTION BY A PARTY | MOT. FOR JUDGMENT AS A MATTER OF LAW | DENIED |
| + | MOTION BY A PARTY | MOT. FOR NEW TRIAL | DENIED |
| + | MOTION BY A PARTY | MOT. FOR NEW TRIAL | DENIED |
| + | MOTION BY A PARTY | MOT. FOR JUDGMENT AS A MATTER OF LAW | DENIED |
| + | MOTION BY A PARTY | MOT. FOR NEW TRIAL | DENIED |
| + | MOTION BY A PARTY | MOT. FOR JUDGMENT AS A MATTER OF LAW | DENIED |
| + | MOTION BY A PARTY | MOT. FOR NEW TRIAL | DENIED |
| + | MOTION BY A PARTY | MOT. FOR NEW TRIAL | DENIED |
| + | MOTION BY A PARTY | MOT. FOR ENHANCED DAMAGES/ATTORNEYS' FEES (§§284-285) | DENIED |
| + | MOTION BY A PARTY | MOT. FOR PRE-JUDGMENT INTEREST | GRANTED |
| + | MOTION BY A PARTY | MOT. FOR POST-JUDGMENT INTEREST | GRANTED |
| + | MOTION BY A PARTY | MOT. FOR JUDGMENT ON FEWER THAN ALL CLAIMS OR PARTIES (FRCP 5 | GRANTED |
| + | N/A | AMENDED JUDGMENT | N/A |
| + | MOTION BY A PARTY | MOT. TO LIFT STAY/REOPEN | GRANTED |
| + | MOTION BY A PARTY | MOT. FOR CONTEMPT (PERMANENT INJUNCTION) | DENIED WITH |

| ID: 56284 | MND | DMN | 0-99-CV-01356 | | TOTAL: | | DONE ▼ |
|---|---|---|---|---|---|---|---|

ANCHOR WALL SYSTEMS V. ROCKWOOD RETAINING, ET AL

DOCKET NUM: 829    FILED 3/31/2009    WEB CASE  WEB .PDF LOCAL .PDF LOCAL .XLS

MEMORANDUM OPINION AND ORDER DENYING DEFENDANTS' 656 MOTION FOR JUDGMENT AS A MATTER OF LAW OR FOR A NEW TRIAL ON THE ISSUE OF INDUCED INFRINGEMENT; DENYING DEFENDANTS' 661 MOTION FOR NEW TRIAL ON INFRINGEMENT OF THE '713 PATENT; DENYING DEFENDANTS' 664 MOTION FOR JUDGMENT AS A MATTER OF LAW OR FOR

KTOW

PATENTS:
REMEDIES: DONE
FILERS: DONE
EVENTS: DONE
DECL'TIONS: DONE
TERMS:
ANNO'TIONS: DONE

| CASE JUDGES | CASE PARTIES/PATENTS | FILERS | EVENTS | REMEDIES | DECLARATIONS | CLAIM TERMS |
|---|---|---|---|---|---|---|

| | RECEPIENT_ID | SUPPLIER_ID | REMEDY_ID | AMOUNT | OVERTURNED: |
|---|---|---|---|---|---|
| + | ANCHOR WALL SYSTEM | ROCKWOOD RETAINI | PRE-JUDGMENT INTEREST | 4923358 | 0 |

*FIG. 11*

| ID: 56284 | MND | DMN | 0-99-CV-01356 | | TOTAL: | DONE |
|---|---|---|---|---|---|---|

ANCHOR WALL SYSTEMS V. ROCKWOOD RETAINING, ET AL

DOCKET NUM: 829    FILED 3/31/2009    WEB CASE  WEB .PDF  LOCAL .PDF  LOCAL .XLS

MEMORANDUM OPINION AND ORDER DENYING DEFENDANTS' 656 MOTION FOR JUDGMENT AS A MATTER OF LAW OR FOR A NEW TRIAL ON THE ISSUE OF INDUCED INFRINGEMENT; DENYING DEFENDANTS' 661 MOTION FOR NEW TRIAL ON INFRINGEMENT OF THE '713 PATENT; DENYING DEFENDANTS' 664 MOTION FOR JUDGMENT AS A MATTER OF LAW OR FOR

KTOW

PATENTS:
REMEDIES: DONE
FILERS: DONE
EVENTS: DONE
DECL'TIONS: DONE
TERMS:
ANNO'TIONS: DONE

| CASE JUDGES | CASE PARTIES/PATENTS | FILERS | EVENTS | REMEDIES | DECLARATIONS | CLAIM TERMS |
|---|---|---|---|---|---|---|

| PATENT_ID | DECLARATION_ID |
|---|---|
| 5709062 | INFRINGED |
| 5704183 | INFRINGED |

*FIG. 12*

| ID: 56284 | MND | DMN | 0-99-CV-01356 | | TOTAL: | DONE |
|---|---|---|---|---|---|---|

ANCHOR WALL SYSTEMS V. ROCKWOOD RETAINING, ET AL

DOCKET NUM: 829     FILED 3/31/2009     WEB CASE   WEB .PDF   LOCAL .PDF   LOCAL .XLS

MEMORANDUM OPINION AND ORDER DENYING DEFENDANTS' 656 MOTION FOR JUDGMENT AS A MATTER OF LAW OR FOR A NEW TRIAL ON THE ISSUE OF INDUCED INFRINGEMENT; DENYING DEFENDANTS' 661 MOTION FOR NEW TRIAL ON INFRINGEMENT OF THE '713 PATENT; DENYING DEFENDANTS' 664 MOTION FOR JUDGMENT AS A MATTER OF LAW OR FOR

KTOW

PATENTS:  
REMEDIES: DONE  
FILERS: DONE  
EVENTS: DONE  
DECL'TIONS: DONE  
TERMS:  
ANNO'TIONS: DONE

| CASE JUDGES | CASE PARTIES/PATENTS | FILERS | EVENTS | REMEDIES | DECLARATIONS | CLAIM TERMS |
|---|---|---|---|---|---|---|

| TERM | DEFINITION | PATENT_ID | PAGE_NUMBER |
|---|---|---|---|
|  |  |  |  |

```
https://www.docketnavigator.com/pdfs/cand-3-04-cv-03526-163.pdf
```

IN THE UNITED STATES DISTRICT COURT

FOR THE NORTHERN DISTRICT OF CALIFORNIA

| | |
|---|---|
| ACCO BRANDS, INC., d/b/a KENSINGTON TECHNOLOGY GROUP. | No. C 04-03526 SI |
| PLAINTIFF, | ORDER GRANTING DEFENDANTS' MOTION FOR LEAVE TO AMEND PRELIMINARY INVALIDITY CONTENTIONS |
| v. | |
| PC GUARDIAN ANTI-THEFT PRODUCTS, INC., and FELLOWES, INC., | |
| Defendants, | |

Defendants have filed a motion for leave to amend their preliminary invalidity contentions. The motion is scheduled for hearing on May 23, 2008. Pursuant to Civil Local Rule 7-1(b), the Court finds the matter appropriate for resolution without oral argument, and hereby VACATES the hearing. Having considered the arguments of the parties and the papers submitted, and for good cause shown, the Court hereby GRANTS defendants' motion.

BACKGROUND

In May 2005, defendants PC Guardian and Fellowes served their Preliminary Invalidity Contentions. On January 19, 2006, the Court stayed the present litigation for a little over a year. In

Docket Navigator

*patent litigation research*

HOME | SEARCH | JOIN | CONTACT | LOGOUT

Docket Search
Annotations for court orders

Legal Issues: Determining Invention/Critical Date (and selected subcategories)
Determining Relevant Prior Art (and selected subcategories)
Experimental Use
Presented action: MSJ- Patent Invalid
Court response: Granted sort by: | EVENT | CASE | JUDGE | COURT | DATE |

---

California Central District (CACD)

The court would not consider a prior art reference for purposes of summary judgement on validity where there were fact issues concerning whether the reference "is relevent to the present invention and would have been known to a person of skill in the art."

BK Lighting Inc v. Vision□ Lighting
2-05-cv-02825 (CACD) 2006-05-10

District Judge Margaret M. Morrow 2008-05-09
Motion for Summary Judgement- Patent Invalid:Granted

Delaware District (DED)

In determining the date of conception, the court "should apply a 'rule of reason'"...(t)hat is, the court should examine, analyze, and evaluate reasonably all pertinent evidence when weighing credibility of the inventor's story. Evidence in the form of documents does not need to be corroborated. Rather, "(o)nly the inventor's testimony requires corroboration before it can be considered."

Solvay S.A. v. Honeywell Specialty Materials LLC et al
1-06-cv-00557 (DED) 2006-09-07

District Judge Sue L. Robinson 2008-12-09
Motion for Summary Judgement- Patent Invalid:Granted "(Plaintiff) did not provide, nor was the court able to find, any authority to support the notion that conception must occur in the United States under §102(g)

Solvay S.A. v. Honeywell Specialty Materials LLC et al
1-06-cv-00557 (DED) 2006-09-07

District Judge Sue L. Robinson 2008-12-09
Motion for Summary Judgement- Patent Invalid:Granted "Even if (Plaintiff's) assertion is correct (that conception must occur within the U.S.), the court concludes that (defendant) conceived the invention at issue in the United States upon receipt of (its foreign contractor's) instructions (on how to make the patented substance), because it was at this point that (defendant) possessed a definite and permanent idea of the complete and operative invention, such that it appreciated the fact of its invention."

Solvay S.A. v. Honeywell Specialty Materials LLC et al
1-06-cv-00557 (DED) 2006-09-07

District Judge Sue L. Robinson 2008-12-09
Motion for Summary Judgement- Patent Invalid:Granted Where both parties filed motions for summary judgment under 35 USC §102(g), addressing priority of invention, "(defendant's) status as an 'inventor' persuant to § 102 (f), is not properly before the court." "Contrasted to derivation, a claim of priority of invention does not question whether the patentee 'invented' the subject matter of the court, but instead focuses on which party first invented the subject matter of the count."

Solvay S.A. v. Honeywell Specialty Materials LLC et al
1-06-cv-00557 (DED) 2006-09-07

District Judge Sue L. Robinson 2008-12-09
Motion for Summary Judgement- Patent Invalid:Granted

Docket Navigator- Patent Litigation Research- Windows Internet Explorer https://www.docketnavigator.com/search/form/determinations

Docket Navigator
*patent litigation research*

HOME | SEARCH | JOIN | CONTENT | LOGOUT  Welcome Dwayne Towell (no client)

Docket Search
Patent determinations

Determination Infringed
Party includes "Microsoft"

sort by: | CASE | JUDGE | COURT | DATE | PATENT | DETERMINATION |

---

2009-04-08
Uniloc USA, Inc., et al v. Microsoft Corp. et al
1-03-cv-00440 (RID) 2003-09-26
2009-04-08
5490216 by Richardson, III Infringed

2008-07-23
Lucent Technologies v. Microsoft Corp
3-06-cv-00684 (CASD) 2006-03-28
District Judge Marilyn L. Huff 2008-07-23
5977971 by Guzak Infringed

2008-06-19
Lucent Technologies: Inc. et al v. Gateway, Inc. et al
3-07-cv-02000 (CASD) 2007-10-16
District Judge Marilyn L. Huff 2008-06-19
4763356 by Day, Jr. Infringed Lucent Technologies: Inc. et al v. Gateway, Inc. et al
3-07-cv-02000 (CASD) 2007-10-16
District Judge Marilyn L. Huff 2008-06-19
5347295 by Agulnick Infringed

2008-06-04
Lucent Technologies v. Microsoft Corp
3-06-cv-00684 (CASD) 2006-03-28
[60]
2008-06-04
5977971 by Guzak Infringed

2008-05-15
Anascape, Ltd v. Microsoft Corp. et al
9-06-cv-00158 (TEXD) 2006-07-31
2008-05-15
6906700 by Armstrong Infringed

2002-03-29
Mass Inst of Tech. et al v. Abacus Software, et al
5-01-cv-00344 (TXED) 2001-12-28
District Judge David Folsom 2002-03-29
4500919 by Schreiber Infringed Mass Inst of Tech. et al v. Abacus Software, et al
5-01-cv-00344 (TXED) 2001-12-28
District Judge David Folsom 2002-03-29
4500919 by Schreiber Infringed 8 items found   What would you like to do?  revise query  return to top  no more results © 2009 HOPKINS BRUCE PUBLISHERS, Corp. □ Terms of Use

*FIG. 24*

Docket Navigator - Patent Litigation Research - Windows Internet Explorer https://www.docketnavigator.com/detail/summary/patent/7436

Docket Navigator
*patent litigation research*

HOME | SEARCH | JOIN | CONTACT | LOGOUT          Welcome Dwayne Towell (no client)

Docket Details
Patent 5347295 invented by Agulnick
Control of a computer through a position-sensed stylus

Quick Facts

STATS
- 2 cases
- 21 construed terms
- 2 determinations
- 4 awards
- 0 injunctions

DATES
- Filing Date    1990-10-31
- Grant Date     1994-09-13

| ABSTRACT | CASES | TERMS | AWARDS | INJUNCTIONS | DETERMINATIONS |

Inventors

Agulnick; Todd (Newton Centre, MA), Carr; Robert (San Francisco, CA), Hoeber; Tony (Woodside, CA), Kaplan; S. Jerrold (San Francisco, CA), Low; David R. (Oakland, CA), Ouye; Michael (Palo Alto, CA)

Inventors

A notebook computer which is controlled by a stylus executing gestures on the computer screen. The stylus and the computer include complementary electronic circuitry by which the proximity of the stylus tip to the computer is sensed. The proximity sensing is used to detect to approach of the stylus tip to the computer screen, and gestural commands are then entered on the screen by moving the stylus. The entry of a command is terminated by removing the stylus tip from proximity with the screen, which is detected by the computer, which then implements the command. Alternative methods of implementing the commands include time-outs and command termination buttons.

Main class

345/156, 345/179, 715/273, 715/863

Other classes

| FIG 29A |
|---|
| FIG 29B |

TO FIG 29B

FROM FIG 29A

AWARDS

A G Design & Associates LLC v. Trainman Lantern Company Inc. et al (3-07-cv-05158) WAWD

| Against | In favor of | award | for |
|---|---|---|---|
| Trainman Lantern Company Inc | A.G. Design & Associates LLC | $7,000,000 | Damages |

Docket Sheet 🗗 Comment 💬 Read order 250 📄

INJUNCTIONS

Lifetime Products, Inc. v. Ningbo Wanxiang Plastics Products Co., Ltd. et al (2-09-cv-00802) NVD

| Against | In favor of | for |
|---|---|---|
| Hangzhou Dali Tools Packing Co., Ltd. | Lifetime Products, Inc. | Injunction |
| Ningbo Wanxiang Plastics Products Co., Ltd. | Lifetime Products, Inc. | Injunction |
| Zhejiang Bestem Furniture, Co., Ltd. | Lifetime Products, Inc. | Injunction |

Docket Sheet 🗗 Comment 💬 Read order 28 📄

CLAIM TERMS

Unitherm Food Systems, Inc. v. Foster Poultry Farms, Inc. (4-09-cv-00154) OKND

| Patent | Inventor | Title | terms construed |
|---|---|---|---|
| 7285299 | Howard | Surface Pasteurization of cooked food products | 5 |

Docket Sheet 🗗 Comment 💬 Read order 69 📄 View terms 🗗

PATENT DETERMINATIONS

Edwards Lifesciences AG et al v. Corevalve Inc. (1-08-cv-00091) DED

| Patent | Inventor | Title | In favor of | determinations |
|---|---|---|---|---|
| 5411552 | Andersen | Valve prothesis for implantation in the body and a catheter for implanting such valve prothesis | | Infringed, Not Invalid |

Docket Sheet 🗗 Comment 💬 Read order 69 📄 Read Order 313 📄

SIGNIFICANT RULINGS

Everpure, LLC v. Selecto, Inc. (2-09-cv-02844) CACD

| Motion to Disqualify Expert | Denied |
|---|---|
| District Judge A. Howard Matz | 2010-04-06 |

| Disqualification of Experts | Plaintiff's motion to disqualify defendant's expert who was the inventor of the patent-in-suit was denied. "At the time of the development of the (patent-in-suit), (the expert's former employer) and (plaintiff) were competitors. Both have since been acquired by the same parent company...(The expert's former employer) has assigned the (patent) to (plaintiff), but (plaintiff) has presented no evidence or authority to support the proposition that the confidential relationship between (the expert's former employer) and (defendant's expert) thereby was extended to (plaintiff)." |
|---|---|

Docket Sheet 🗗 Comment 💬 Read order 93 (p. 4, 5) 📄

*FIG. 29B*

COMPUTER-IMPLEMENTED SYSTEMS AND METHODS FOR ANALYZING COURT ACTIVITY

CROSS-REFERENCE TO RELATED APPLICATIONS

This application claims benefit under 35 U.S.C. §119(e) to U.S. Provisional Application No. 61/175,689, filed May 5, 2009, and U.S. Provisional Application No. 61/225,089, filed Jul. 13, 2009, each of which is incorporated herein by reference.

BACKGROUND OF THE INVENTION

Various legal research software and database systems exist to assist people in locating court documents of interest. Lexis-Nexis® and Westlaw® are two such widely-used systems. Users of these systems spend time formulating queries to locate court documents of interest. These systems typically allow users to search for court documents of interest by performing text searches of the contents of such documents and according to limited additional criterion. Once the query results are provided to a user, the user must peer inside each document to understand the specifics of a document, such as, in the case of a court order, the procedural vehicle that prompted the court to enter such an order, the rationale supporting such order, or the results of the order. Such an approach is inadequate for more in-depth type searches or for generating or analyzing relevant statistics and may result in inaccurate and/or incomplete search results.

BRIEF SUMMARY OF THE INVENTION

In accordance with a first aspect, the present invention is directed to a method, on one or more servers comprising one or more computers connected to a network, of analysis and presentation of court document information, the method comprising: at least one of the one or more servers providing, to a user, a user interface, the user interface permitting assignment, for each court ruling associated with a court document stored in a searchable database, of one or more of pre-defined categories relating to the ruling, the one or more pre-defined categories including at least one of: (a) a type of procedural vehicle that led to the ruling; (b) a description of the procedural vehicle that led to the ruling; and (c) the court's ruling; and at least one of the one or more servers arranging the categorized court rulings in the searchable database, such that the court documents can be searched on the basis of at least one or more of the assigned pre-defined categories.

In another aspect, the method further comprises: at least one of the one or more servers sending a query to a court document server requesting new or changed data since a previous such query was processed, the query being structured such that: (a) for a case for which a case record does not exist in the searchable database, a server creates a new case record for the case, a server retrieves docket sheet information for the case comprising one or more of: (i) electronic copies of court documents filed in the case, (ii) docket entries, (iii) party information, (iv) attorney information, and (v) law firm information, and a server adds the docket sheet information to the new case record in the searchable database; and (b) for a case for which a case record exists in the searchable database, a server retrieves a case record for the case, a server updates the docket sheet information for the case, and a server adds the updated docket sheet information to the case record in the searchable database.

In another aspect, the method further comprises, in response to receipt of a query to the searchable database, at least one of the one or more servers providing a viewable search result arranged in relation to the at least one pre-defined category.

In another aspect, the user interface is a graphical user interface.

In another aspect, at least one of the one or more servers arranges the categorized court rulings in the searchable database, such that the court documents can be searched on the basis of one or more categories of docket sheet information comprising one or more of: (i) electronic copies of court documents filed in the case, (ii) docket entries, (iii) party information, (iv) attorney information, and (v) law firm information.

In another aspect, the searchable database is searchable on the basis of at least one or more of the assigned pre-defined categories and one or more categories of docket sheet information comprising one or more of: (i) electronic copies of court documents filed in the case, (ii) docket entries, (iii) party information, (iv) attorney information, and (v) law firm information.

In another aspect, the method further comprises at least one of the one or more servers generating and distributing an electronic newsletter, the newsletter comprising at least one or more of the predefined categories relating to at least one case.

In accordance with another aspect, the present invention is directed to a court document analysis and presentation system, the system comprising: one or more servers comprising one or more computers connected to a network, the one or more servers being configured to: provide, to a user, a user interface, the user interface permitting assignment, for each court ruling associated with a court document stored in a searchable database, of one or more of pre-defined categories relating to the ruling, the one or more pre-defined categories including at least one of: (a) a type of procedural vehicle that led to the ruling; (b) a description of the procedural vehicle that led to the ruling; and (c) the court's ruling; and arrange the categorized court rulings in the searchable database, such that the court documents can be searched on the basis of at least one or more of the assigned pre-defined categories.

In another aspect, the one or more servers are configured to: send a query to a court document server requesting new or changed data since a previous such query was processed, the query being structured such that: (a) for a case for which a case record does not exist in the searchable database, a server creates a new case record for the case, a server retrieves docket sheet information for the case comprising one or more of (i) electronic copies of court documents filed in the case, (ii) docket entries, (iii) party information, (iv) attorney information, and (v) law firm information, and a server adds the docket sheet information to the new case record in the searchable database; and (b) for a case for which a case record exists in the searchable database, a server retrieves a case record for the case, a server updates the docket sheet information for the case, and a server adds the updated docket sheet information to the case record in the searchable database.

In another aspect, the one or more servers are further configured to, in response to receipt of a query to the searchable database, provide a viewable search result arranged in relation to the at least one pre-defined category.

In another aspect, the user interface is a graphical user interface.

In another aspect, the one or more servers are configured to arrange the categorized court rulings in the searchable database, such that the court documents can be searched on the basis of one or more categories of docket sheet information comprising one or more of: (i) electronic copies of court documents filed in the case, (ii) docket entries, (iii) party information, (iv) attorney information, and (v) law firm information.

In another aspect, the searchable database is searchable on the basis of at least one or more of the assigned pre-defined categories and one or more categories of docket sheet information comprising one or more of: (i) electronic copies of court documents filed in the case, (ii) docket entries, (iii) party information, (iv) attorney information, and (v) law firm information.

In another aspect, the one or more servers are configured to generate and distribute an electronic newsletter, the newsletter comprising at least one or more of the predefined categories relating to at least one case.

In yet another aspect, the present invention is directed to a computer-readable storage medium storing a program that, when run by one or more servers comprising one or more computers connected to a network, causes the one or more servers to perform the following steps: providing, to a user, a user interface, the user interface permitting assignment, for each court ruling associated with a court document stored in a searchable database, of one or more of pre-defined categories relating to the ruling, the one or more pre-defined categories including at least one of: (a) a type of procedural vehicle that led to the ruling; (b) a description of the procedural vehicle that led to the ruling; and (c) the court's ruling; and arranging the categorized court rulings in the searchable database, such that the court documents can be searched on the basis of at least one or more of the assigned pre-defined categories.

In yet another aspect, the steps further comprise: sending a query to a court document server requesting new or changed data since a previous such query was processed, the query being structured such that: (a) for a case for which a case record does not exist in the searchable database, a server creates a new case record for the case, a server retrieves docket sheet information for the case comprising one or more of: (i) electronic copies of court documents filed in the case, (ii) docket entries, (iii) party information, (iv) attorney information, and (v) law firm information, and a server adds the docket sheet information to the new case record in the searchable database; and (b) for a case for which a case record exists in the searchable database, a server retrieves a case record for the case, a server updates the docket sheet information for the case, and a server adds the updated docket sheet information to the case record in the searchable database.

In another aspect, the steps further comprise, in response to receipt of a query to the searchable database, providing a viewable search result arranged in relation to the at least one pre-defined category.

In another aspect, the user interface is a graphical user interface.

In another aspect, the searchable database is searchable on the basis of at least one or more of the assigned pre-defined categories and one or more categories of docket sheet information comprising one or more of: (i) electronic copies of court documents filed in the case, (ii) docket entries, (iii) party information, (iv) attorney information, and (v) law firm information.

In another aspect, the steps further comprise generating and distributing an electronic newsletter, the newsletter comprising at least one or more of the predefined categories relating to at least one case.

BRIEF DESCRIPTION OF THE DRAWINGS

The figures are for illustration purposes only and are not necessarily drawn to scale. The invention itself, however, may best be understood by reference to the detailed description which follows when taken in conjunction with the accompanying drawings in which:

FIG. 4 is an example of a graphical user interface (GUI) showing the pre-defined categories;

FIG. 6 is an exemplary GUI representing a docket sheet that allows a user to identify which document descriptions have been received;

FIG. 7 is an exemplary GUI that allows records to be created and/or edited, in accordance with an aspect of the present invention;

FIG. 8 is a view of the GUI in FIG. 7 with the Filers tab selected;

FIG. 9 is a view of the GUI in FIG. 7 with the Events tab selected;

FIG. 10 is a view of the GUI in FIG. 9 with a legal vehicle record expanded to allow for annotations to be associated with each legal vehicle;

FIG. 11 is a view of the GUI in FIG. 7 with the Remedies tab selected;

FIG. 12 is a view of the GUI in FIG. 7 with the Declarations tab selected;

FIG. 13 is a view of the GUI in FIG. 7 with the Claim Terms tab selected;

FIG. 16 is a screen shot illustrating an example of search results that satisfy input search terms;

FIG. 17 is an illustration of an exemplary document that is displayed in response to clicking the PDF icon shown in FIG. 16;

FIG. 18 is a screen shot illustrating search results with annotations shown;

FIG. 20 is a screen shot of a GUI showing search results;

FIG. 21 is a screen shot of a GUI showing search results arranged primarily by court;

FIG. 23 is a screen shot of a GUI showing exemplary search results that satisfy search criteria in a patent determinations search;

FIG. 24 is a screen shot of a GUI showing exemplary search results that satisfy search criteria in a patent determinations search arranged primarily by date;

FIG. 25 illustrates docket details including the Abstract related to a patent whose search results were shown in FIG. 24;

FIG. 26 illustrates docket details including the claim terms related to a patent whose search results were shown in FIG. 24;

FIG. 27 illustrates docket details including awards related to a patent whose search results were shown in FIG. 24;

FIG. 28 illustrates docket details including determinations related to a patent whose search results were shown in FIG. 24.

DETAILED DESCRIPTION OF THE INVENTION

Figure 1:
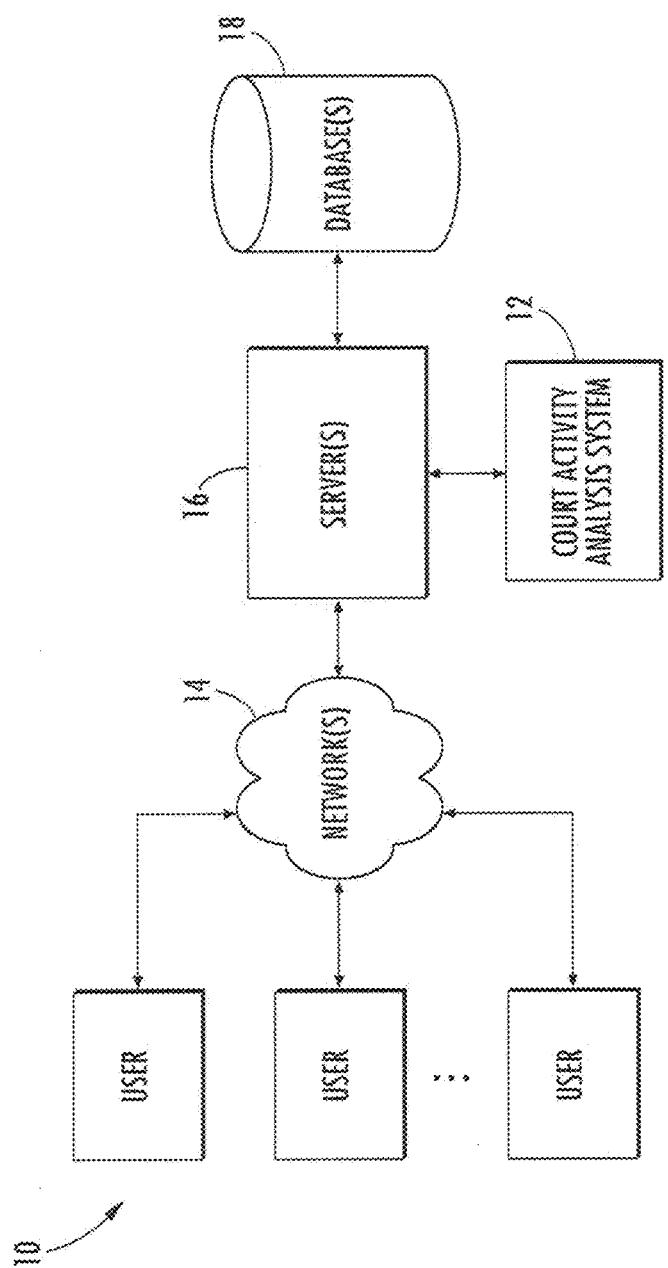
FIG. 1 is a diagram depicting the environment in which the court activity analysis system operates.

FIG. 1 depicts at an environment wherein users 10 can interact with a court activity analysis system 12. The court activity analysis system 12 is preferably implemented as software that runs on a server or servers, such as server(s) 16. The court activity analysis system 12 provides users with detailed court activity information about multiple court cases. For example, as will be developed below, a user can search for a judge's track record with respect to granting or denying certain types of motions. This is in contrast to systems that only scan the full text of court documents and do not apply any categorization/classification at a granular level of detail. The servers preferably comprise one or more computers configured, e.g., programmed, to perform the algorithms set forth below.

In accordance with a preferred embodiment, a user can interact with the court activity system in a number of ways, such as over one or more networks 14. Server(s) 16 accessible through the network(s) can host the court activity analysis system 16. One or more data stores (e.g., database(s)) 18, can store the data to be analyzed by the system as well as any intermediate or final data generated by the system.

The court activity analysis contains detailed information about significant court documents that are generated with respect to a legal proceeding. During a legal proceeding, a dispute resolution tribunal, such as a federal or state trial court in the United States or an administrative court such as the United States International Trade Commission, maintains a written record of events that occur with respect to each dispute. This written record, commonly called a "docket," includes written submissions by the parties to the dispute, as well as written directives by the court.

Courts also maintain a set of procedural rules that describe and/or regulate the use of pleadings, applications, petitions, and motions that may be used to seek relief from the court. (As used herein, pleadings, applications, petitions, and motions are referred to herein as procedural vehicles.) Each written submission by a party may include one or more such procedural vehicle(s) requesting that the court take some action. For example, a pleading procedural vehicle might request that the court grant the party's ultimate relief such as a permanent injunction, a declaration, or a damages award. As a further example, a motion in limine procedural vehicle might request that the court exclude certain evidence from its decision on the merits of the dispute. Each order by a court may be in response to a party's submission, in response to an external event, or upon the court's own initiative. Moreover, each order may contain one or more rulings such as an order granting or denying a party's motion.

Figure 2:
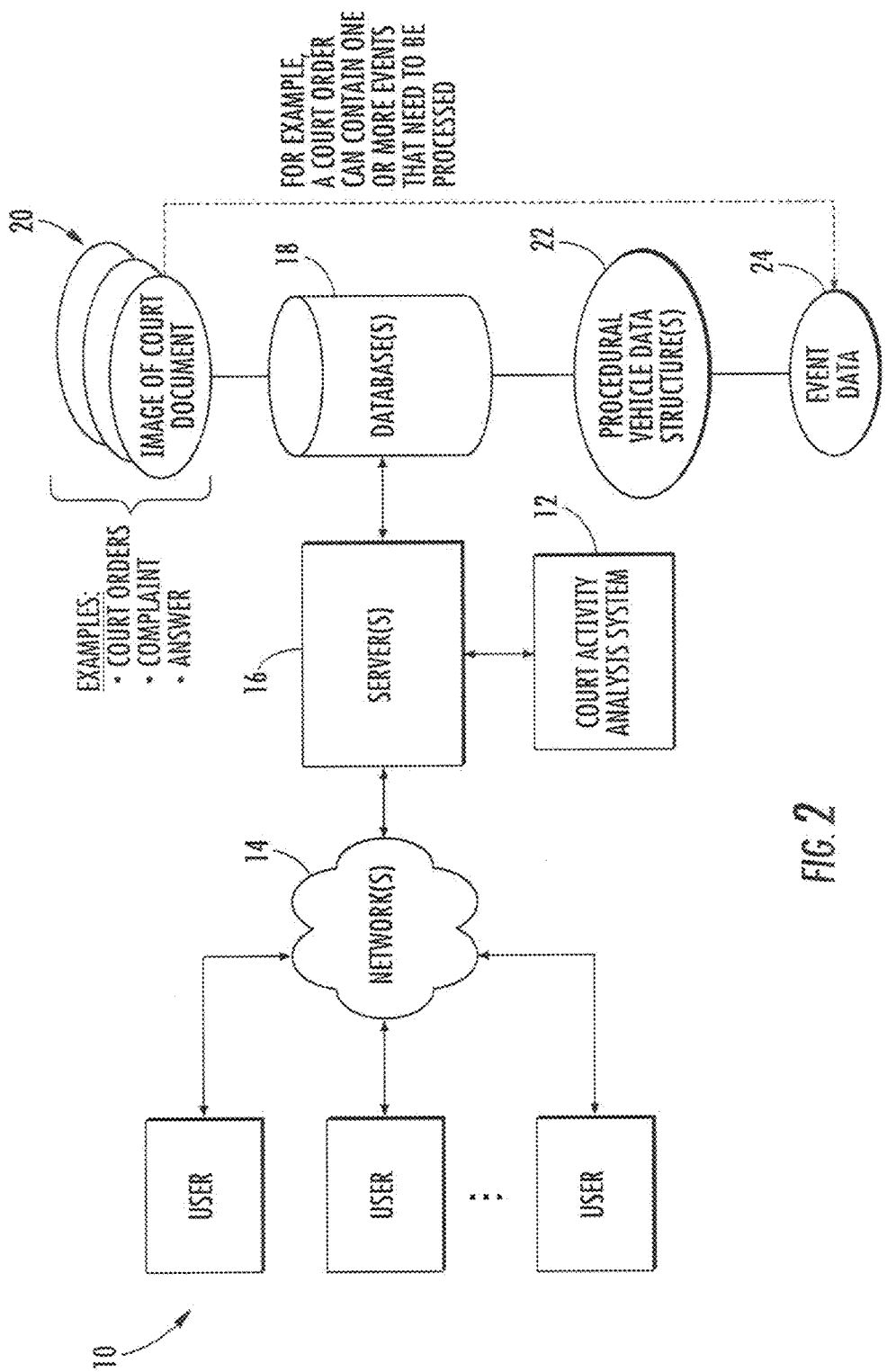
FIG. 2 is a diagram showing the environment shown in FIG. 1 together with procedural vehicle data structures.

As shown in FIG. 2, the court activity analysis system can include one or more procedural vehicle data structure(s) to capture information about events in that occur during a legal proceeding which are recorded in significant court documents. For example, the one or more events that are related to a court document (e.g., a court order) 20 can be captured and stored in the procedural vehicle data structure(s) 22 as event data 24.

Figure 3:
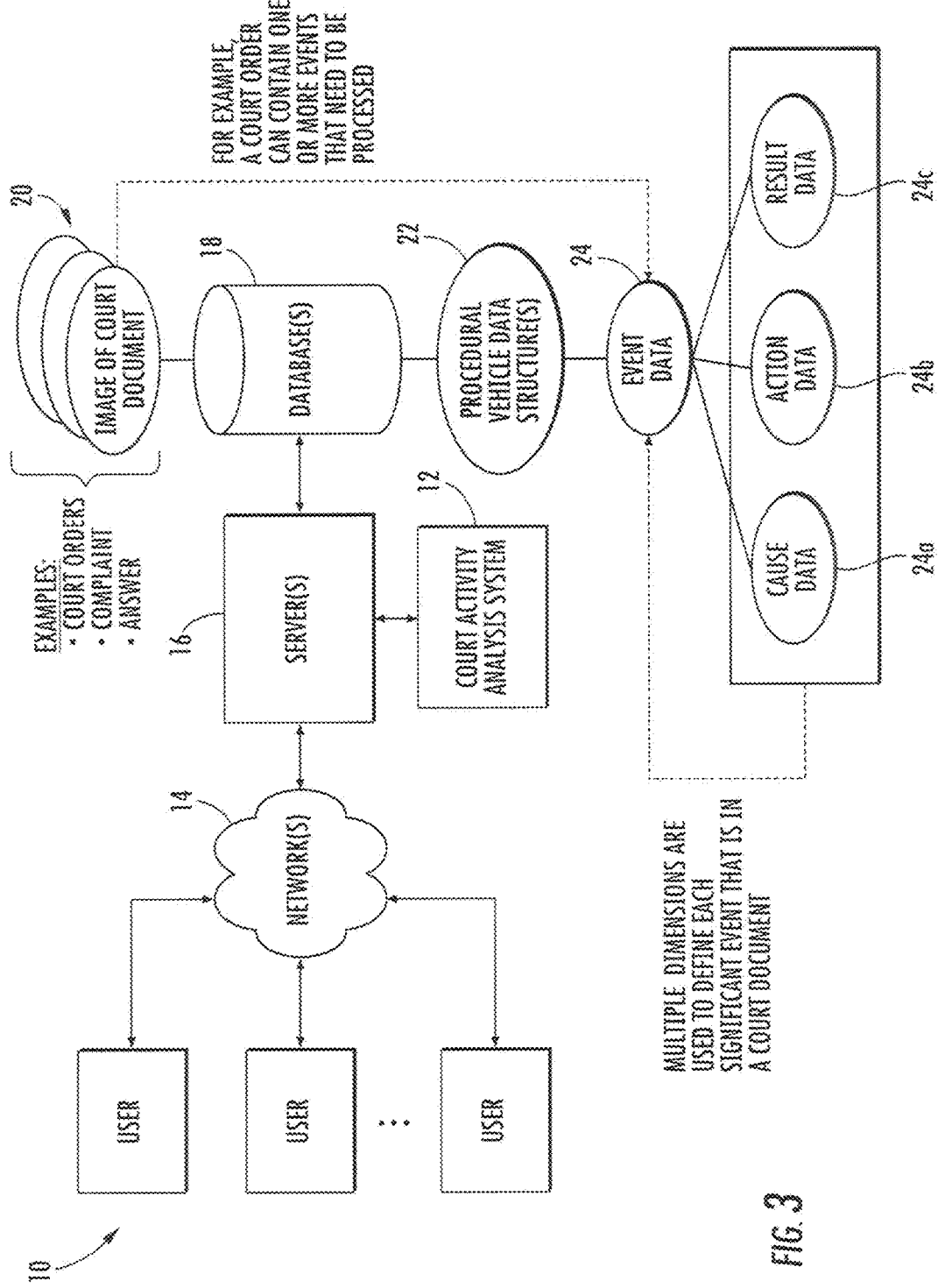
FIG. 3 is a diagram showing the pre-defined categories to which a court's rulings can be assigned.

As shown in FIG. 3, events can be analyzed by assigning, for each ruling contained in a court order, one or more of the following pre-defined categories: (i) type of procedural vehicle that led to the court's ruling (sometimes referred to as a "cause" and illustrated in FIG. 3 as Cause Data 24a), (ii) description of the procedural vehicle that led to the court's ruling (sometimes referred to as an "action" and illustrated in FIG. 3 as Action Data 24b), and (iii) the court's ruling (sometimes referred to as a "result" and illustrated in FIG. 3 as Result Data 24c). A sample set of pre-defined categories for causes, actions and results that are typical in patent infringement litigation in United States District Courts may be found in Tables 1, 2, and 3, respectively.

TABLE 1

| "Cause" (or Type of Procedural Vehicle) |
| --- |
| Motion by a Party |
| Ex Parte/Emergency Motion by a Party |
| Stipulation/Agreed/Unopposed Motion |
| Motion to Reconsider |
| Renewed Motion |
| Motion to Clarify Order Re |
| Motion to Modify |
| Motion to Vacate |
| Report by Magistrate Re |
| Report by Special Master Re |
| Objection to Order of Magistrate Judge Re |
| Objection to Special Master's Order/Report Re |
| Sua Sponte (Court's Motion) |
| Ruling on Evidence Presented at Trial or Hearing |
| Remand |

TABLE 2

| "Action" (or Description of Procedural Vehicle) |
| --- |
| Complaint |
| Amended Complaint |
| Complaint in Intervention |
| Answer |
| Amended Answer |
| Counterclaim |
| Amended Counterclaim |
| Crossclaim |
| Amended Crossclaim |
| Mot. To Substitute Parties |
| Mot. to Enlarge Time to Answer |

TABLE 2-continued

"Action" (or Description of Procedural Vehicle)

Mot. to Proceed In Forma Paupens
Mot. to Reassign/Recuse Judge
Entry of Default
Default Judgment
Mot. to Set Aside Default/Dismissal
Mot. to Intervene
Mot. to Compel Arbitration/Mediation
Mot. for Leave to File Amended or Supplemental Pleading
Mot. for Leave to File 3rd Party Pleading
Mot./Application for Temporary Restraining Order
Mot./Application for Preliminary Injunction
Mot. To Modify Preliminary Injunction
Mot. for Contempt (TRO or Preliminary Injunction)
Order re Contempt (not relating to TRO or injunctions)
Mot. For Sanctions (other than discovery)
Mot. to Remand
Mot. to Strike Pleading
Mot. to Strike Non-Pleading Filing
Mot. to Dismiss - Lack of Standing to Assert Patent Claims
Mot. to Dismiss - Lack of Subject Matter
Mot. to Dismiss - Lack of Personal Jurisdiction
Mot. to Dismiss - Improper Venue
Mot. to Dismiss - Failure of Process
Mot. to Dismiss - Failure of Service of Process
Mot. to Dismiss - Failure to Plead with Particularity (FRCP 9)
Mot. to Dismiss - Failure to State a Claim
Mot. to Dismiss - Failure to Join an Indispensible Party
Mot. to Dismiss - Failure to Prosecute
Mot. to Dismiss - Other
Mot. to Dismiss - Pursuant to Parties Agreement
Covenant Not to Sue
Stipulation
Mot. for Judgment on the Pleadings
Mot. for More Definite Statement
Mot. to Join Necessary Party
Mot. for Stay Pending Reexamination
Mot. for Stay Pending interference
Mot. for Stay Pending Investigation by ITC
Mot. for Stay Pending Arbitration
Mot. for Stay Pending Settlement
Mot. for Stay Pending Interlocutory Appeal/Mandamus
Mot. for Stay Pending Resolution of Related Action
Mot. for Stay Pending Decision by MDL Panel
Mot. for Stay Pending Bankruptcy
Mot. to Stay Discovery
Mot. to Stay - Other
Mot. re First-to-File Rule
Mot. to Lift Stay/Reopen
Mot. to Transfer Venue - Convenience
Mot. to Transfer Venue - MDL Proceeding
Mot. to Transfer Venue - Other
Mot. to Exceed Page Limits
Mot. for Continuance of Hearing Date
Mot. to Expedite Hearing
Mot. for Hearing/Oral Argument
Mot. to Modify Briefing Schedule
Mot. for Leave to File Sur-Reply or other Additional Brief
Mot. To Relate Case
Mot. to Consolidate
Mot. to Consolidate/Transfer to MDL
Mot. to Sever
Mot. to Bifurcate
Scheduling/Pretrial Order (Rule 16)
Mot. to Modify Scheduling/Pretrial Order
Mot. for Expedited Discovery
Mot. for Discovery in Excess of Limits
Appointment of Special Master
Review of Magistrate's Order
Mot. for Protect. Order - Relief from Discovery
Mot. for Protect. Order - Preserve Confidentiality
Mot. to File Under Seal
Mot. to Enforce Protective Order
Mot. for Relief from Protective Order
Mot. To Preclude Disclosure of Confidential Information
Mot. to Change Discovery Response
Mot. to Compel Discovery
Mot. Concerning Privilege/Work Product
Mot. for Discovery Sanctions - Monetary
Mot. for Discovery Sanctions - Issue/Evidence
Mot. for Discovery Sanctions - General/Unspecified
Application for Letters Rogatory
Mot. to Shift Cost of Discovery
3rd Party Discovery - Motion to Quash
3rd Party Discovery - Motion to Compel
Mot. to Disqualify Expert
Mot. to Strike Expert Reports
Mot. to Strike Expert Designations
Mot. to Strike Contentions Under Local Patent Rules
Mot. to Strike/Exclude Evidence Submitted With Motion
Mot. for Leave to Serve Amended Contentions Under Local Patent Rules
Mot. for Late Designation of Experts
Mot. to Amend Expert Reports/Serve Expert Reports Late
Mot. to Amend/Correct Discovery Response
Mot. to Reopen Discovery
Mot. To Correct "Obvious Error" in Patent
Mot. Re Claim Construction
Mot. to Limit Number of Claims
Mot. to Increase Number of Claims
Claim Construction (Markman)
Mot. to Appoint Special Master for Claim Construction
Report of Special Master for Claim Construction
Court's Adoption of Report of Special Master for Claim Construction
Mot. to Appoint Technical Advisor
Mot. for Leave to File Summary Judgment Motion
MSJ - Infringement
MSJ - Noninfringement
MSJ - Patent Invalid
MSJ - Patent Not Invalid
MSJ - Patent Unenforceable
MSJ - Patent Not Unenforceable
MSJ - Willful Infringement
MSJ - No Willful Infringement
MSJ - Lack of Standing
MSJ - No Lack of Standing
MSJ - Re Damages
MSJ - To Establish Priority Date
MSJ - Claim/Defense Barred by Prior Agreement
MSJ - Claim/Defense Not Barred by Prior Agreement
MSJ - Claim/Defense Barred by SOL, Laches, Estoppel
MSJ - Claim/Defense Not Barred by SOL, Laches, Estoppel
MSJ - Other
Mot. to Stay/Continue Summary Judgment (FRCP 56(f) )
Mot. for Judgment as a Matter of Law
Mot. to Withdraw as Counsel
Mot. to Disqualify Counsel
Mot. to Quash Trial Subpoena
Mot. in Limine - Expert Testimony
Mot. in Limine - Fact Witness/Evidence/Exhibits
Mot. in Limine - Statements by Counsel
Mot. In Limine - Evidence Supporting Claim/Defense
Mot. to Strike Evidence Presented at Trial
Mot. Re Pre-Trial Disclosures
Mot. Re Trial Procedure
Pretrial Order
Mot. Re Jury Instructions
Findings of Fact and Conclusions of Law
Verdict
Mot. for New Trial
Mot. For Remittitur
Mot. for Certification of Order for Interlocutory Appeal (28 USC § 1292(b))
Mot. for Judgment on Fewer Than All Claims or Parties (FRCP 54(b))
Mot. for Judgment
Judgment
Amended Judgment
Mot. to Amend/Reopen Record
Mot. for Permanent Injunction
Mot. For Ongoing Royalty
Mot. for Damages
Mot. for Accounting
Mot. For Pre-Judgment Interest
Mot. for Post-Judgment Interest
Mot. for Relief from Judgment (FRCP 60)

TABLE 2-continued

"Action" (or Description of Procedural Vehicle)

Mot. to Modify Judgment - Injunction
Mot. to Modify Judgment - Damages
Mot. to Modify Judgment - Other
Mot. for Enhanced Damages/Attorneys' Fees (§§ 284-285)
Mot. for Sanctions Under FRCP II
Mot. for Sanctions Under 28 USC § 1927
Mot. for Sanctions Per Court's Inherent Power
Mot. to Stay Injunction and/or Execution of Judgment
Mot. to Vacate Prior Order
Mot. for Enforcement of Judgment
Mot. to Enforce Settlement Agreement
Mot. for Contempt (Permanent Injunction)
Mot. for Post-Judgment Discovery
Bill of Costs
Clerk's Order/Memo Re Costs
Mot. Re Costs
Mot. for Extension of Time to Appeal (FRAP 4)
Opinion/Remand from CAFC

TABLE 3

"Result"(or Tribunal Ruling)

Denied
Denied Without Prejudice
Rec'md Denial
Granted
Rec'md Granting
Denied In Part, Granted in part
Rec'md Denying in Part, Granting in Part
Denied as Moot
Taken Under Advisment
Stricken
Stricken Without Prejudice
Vacated
Adopted
Rejected
Adopted in Part, Rejected in Part
Objection Overruled/Report Adopted
Sustained
Judgement Reserved
Rfr'd to Special Master
Rfr'd to Magistrate Judge
Continued Pending Completion of Discovery Different pre-defined categories may be appropriate for other types of disputes or disputes pending in other tribunals. Additionally, such pre-defined categories need to be updated periodically to account for changes in the tribunal's rules and/or decisions concerning those rules.

As additional examples of the categorization described above, if a party to a dispute filed a motion to compel discovery responses and the court filed an order containing a single ruling granting that motion, such order could be categorized as follows:

FIRST RULING

| | |
|---|---|
| Cause: | Motion by a Party |
| Action: | Mot. to Compel Discovery |
| Result: | Granted |

As a further example of the categorization described above, if a party to a dispute filed a motion for summary judgment of noninfringement and a motion for summary judgment of patent invalidity and the tribunal denied both motions in a single written order, such order could be categorized as follows:

FIRST RULING

| | |
|---|---|
| Cause: | Motion by a Party |
| Action: | MSJ - Noninfringement |
| Result: | Denied |

SECOND RULING

| | |
|---|---|
| Cause: | Motion by a Party |
| Action: | MSJ - Patent Invalid |
| Result: | Denied |

FIG. 4 is an exemplary screen shot that shows how the categorization of a tribunal's written directive may be accomplished using a graphical user interface. As would be clear to one of ordinary skill in the art, display of the court data in the manner shown in this and the following figures can be effected using any of a number of known software tools. For example, database client software with customizable tools, such as Microsoft Access, OpenOfficeBase or Navicat could be employed. Alternatively, Web server based solutions such as phpMyAdmin, phpPgAdmin, or custom server-based code could be employed to create a display of the data. Another tool that could be used is office productivity software, such as Microsoft Excel or OpenOfficeCalc in combination with data extraction routines such as Microsoft Visual Basic or Javascript. Of course the invention is not limited to any particular manner of providing the graphical user interface.

Figure 5:
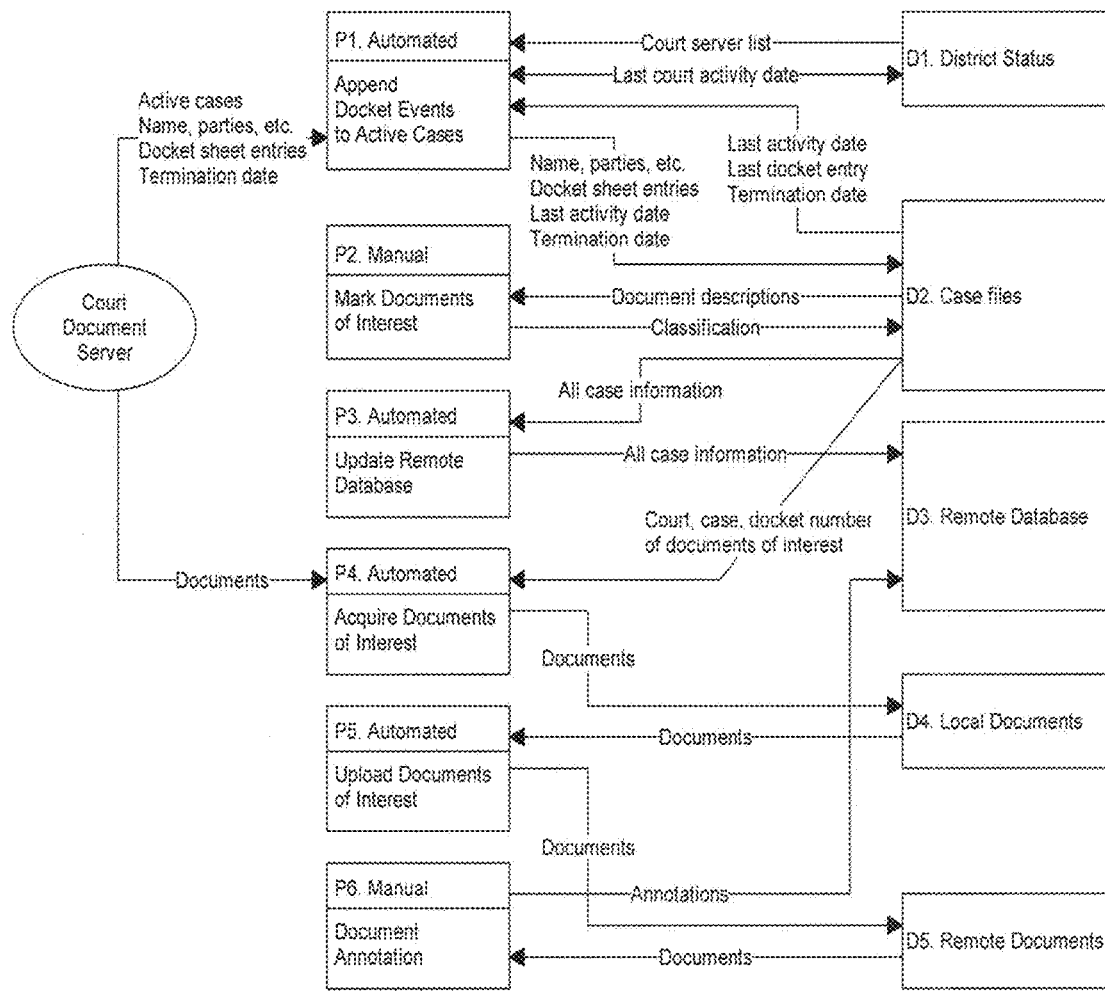
FIG. 5 is a diagram depicting a process for generating the contents of a court activity analysis database in accordance with an aspect of the present invention.

The contents (e.g., cause, action, and result data) of the court activity analysis database can be generated in different ways. FIG. 5 depicts a process for retrieving data from different databases and transforming the data for insertion into the court activity analysis database and is described below.

With reference to FIG. 5, an automated process (P1) is executed on an application server to query each court document server (such as the United States Judiciary's Public Access to Court Electronic Records database commonly referred to as "PACER") to determine which cases have exhibited activity. This query is limited to cases with activity since the last date the cases in that court were successfully updated. The last successful update date for each district is maintained in D1.

For each case found with new activity, a query is performed to return docket entries that are after the last known docket entry. Any new docket entries are appended to a case record (D2). If a case that does not already exist in D2 is found due to activity, a new case record is created and all docket entries are appended to the record.

After appending docket events as described above, new cases and cases with new docket entries are identified and potentially marked as "of interest" (P2). For each case, a user interface is provided to facilitate a person reading the docket sheet description of the court documents to determine if the document is of interest for annotation or other reasons. A document can be identified of interest based upon many different criteria, such as whether the document is a court order. In general, the criteria can specify that primarily court orders (e.g., where court decisions are rendered) as well as principal documents (e.g., complaints and answers) are marked as "of interest." This allows a person with no or little legal training to handle this particular data processing phase.

To facilitate the identification process, the user interface is configured to allow a user to use a marker or other indicia to identify which document descriptions have already be reviewed. An example docket sheet is shown in FIG. 6. In the example docket sheet of FIG. 6, from case Texas Southern District 4:07-cv-02392, the red background in cell D139 indicates where reviewing stopped. The shading indicates that document 134, an order denying Motion for Leave to File Sur-Reply, is a document of interest. In this operational scenario, it would have been identified as a document of interest because the document does not contain mere requests for a particular ruling by the judge, but contains the actual ruling result given by a judge.

After completing the manual process of marking documents of interest as described above, an automated process on an application server (P4) is used to download the documents. For each case with newly marked documents, the process queries the court server and retrieves the requested document as a .PDF file, temporarily storing it locally (D4). After retrieving all requested documents, new PDF files are replicated (P5) on a server search application (D5) for review and later presentation.

After completing the manual process of marking documents of interest as described above, an automated process on an application on the server (P3) is used to synchronize the search application server database (D3) with the local case records (D1). The information synchronized includes new cases, new docket entries, parties, representatives, and other case information available from the court website.

After completing database synchronization and acquiring documents of interest as described above, a manual process (P6) is used to add additional case information, classification, tags, and annotations. Using a database form in the form of a graphical user interface, records are edited and/or created to capture the additional information. An example of such an interface is shown in FIG. 7. For example, information about document 829 from case 0:99-cv-01356 in the Montana District is shown in FIG. 7. The top portion of the interface shown in FIG. 7 presents information about the case and document, below a user-comment field are tab interface items, as indicated by 70 in the figure, which are used to select the part of the case or document to be edited.

Selecting the "Case Judges" tab allows the user to enter judges and their roles on the case under review. In this example, David S. Doty, John R. Tunheim, and Franklin L. Noel have been entered as judicial officers involved in the case.

Figure 7A:
FIG. 7a is a view of the GUI in FIG. 7 with the Case Parties/Patent tab selected.

Selecting the "Case Parties/Patents" tab allows the user to enter parties and the patents they are asserting, as shown in FIG. 7a. In this example; six parties have been entered as participants in the case. The "boxed plus" interface item allows patents to be associated with a party of the case. In the example above, seven patents have been entered as patents being asserted by the party "Anchor Wall Systems".

Selecting the "Filers" tab allows the user to identify which party, parties, or judge filed the document, as shown in FIG. 8. In this example, District Judge John R. Tunheim has been entered as the filer of the document.

Selecting the "Events" tab allows the user to identify the specific legal vehicles involved in the document, as shown in FIG. 9. In the example shown in FIG. 9, fifteen separate legal vehicles were identified and related to the document under review, including five motions for a new trial and three motions for judgment as a matter of law. In addition to the legal vehicle (labeled as an "action" in this example interface), the cause and result of each legal vehicle is recorded.

Figure 10:
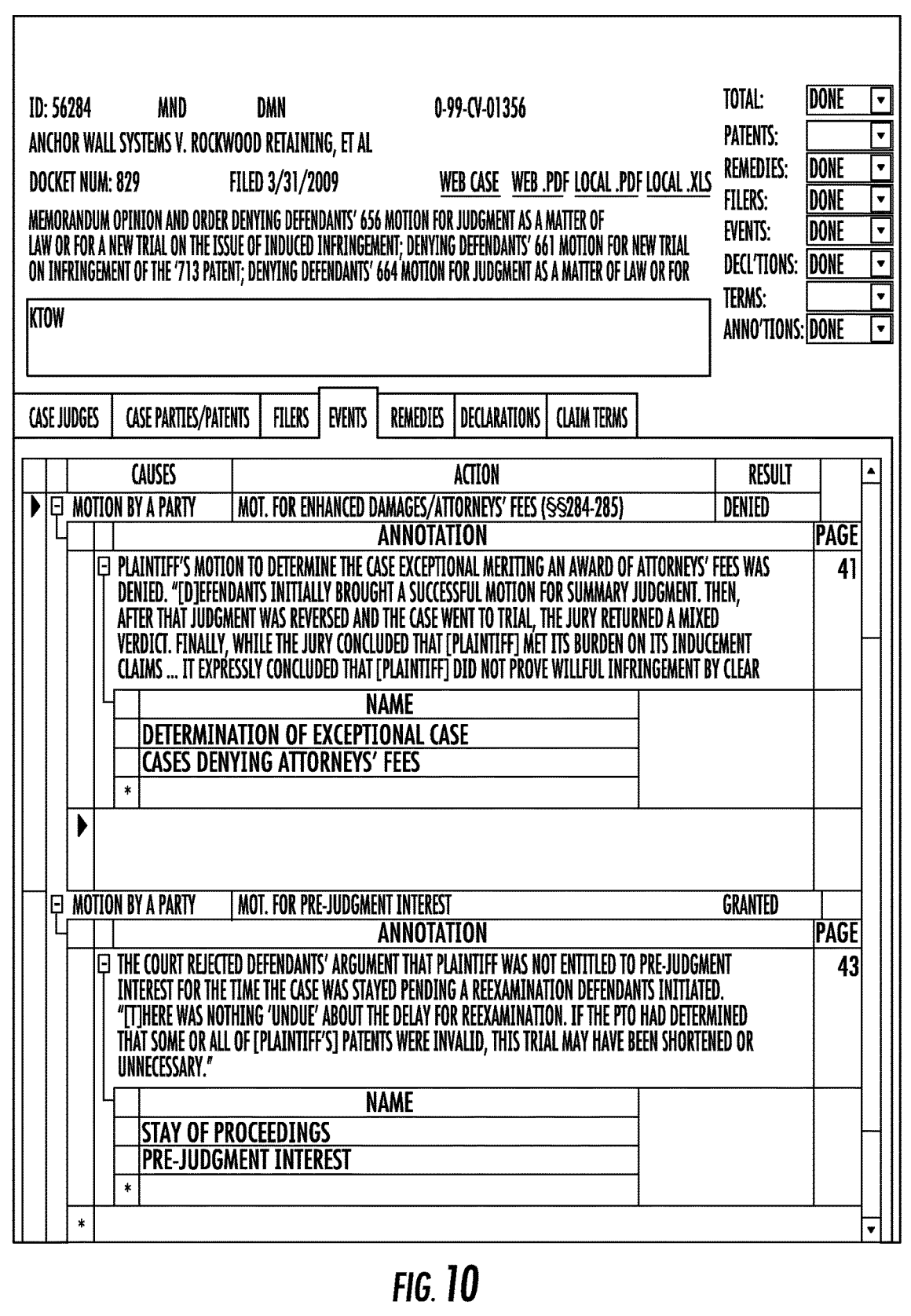

The "boxed plus" interface item next to each legal vehicle record allows annotations to be associated with each legal vehicle, as shown in FIG. 10. In the example shown in FIG. 10, two annotations have been entered. The first annotation is in relationship to the legal vehicle "Motion for Enhanced Damages/Attorney's Fees", which was made by a party and subsequently denied. The annotation had further been identified as relating to text on page 41 of the document and involving the legal issues "Determination of Exceptional Case" and "Cases Denying Attorney's Fees". The second annotation is in response to the "Motion for Pre-judgment Interest" made by a party and subsequently granted. The annotation is further identified as related text from page 43 of the document and involving "Stay of Proceedings" and "Pre-judgment Interest".

Selecting the "Remedies" tab allows the user to identify the specific legal remedies imposed by the document, as shown in FIG. 11. In the example shown in FIG. 11, the user has entered an amount of $4,923,358.00 as Pre-judgment Interest to be paid by Rockwood Retaining Walls, Inc. to party Anchor Wall Systems.

Selecting the "Declarations" tab allows the user to identify specific determinations made by the court with respect to specific patents in the case, as shown in FIG. 12. In the example shown in FIG. 12, the user has entered that patents 5709062 and 5704183 were both determined to have been infringed.

Finally, selecting the "Claim Terms" tab, as shown in FIG. 13, allows the user to enter specific claim terms defined by the court. In the example illustrated in FIG. 13, no claim terms were defined by the court so no information was entered. However, were terms defined, a user could enter the term, its definition, the patent number from with the term was taken, and the page number in the court document where the definition began.

An automated process retrieves patent information including a PDF of the patent document itself. A process on an application server determines which patents have incomplete information. For each of these patents, the USPTO website is queried and information such as the inventor, issue date, title, etc. are used to populate the search application server database. In addition, the individual pages of the patent are downloaded as TIFF files and assembled into a PDF which is stored on the search application server for later reference and/or presentation. As would be understood by those skilled in the art, extracting the information from the USPTO website can be done by any known method of extracting such website data, or equivalents now known or developed in the future.

It should be understood that similar to the other processing flows described herein, the steps and the order of the steps in these operational scenarios flowchart described herein may be altered, modified, removed and/or augmented and still achieve the desired outcome. For example, the above-described process illustrated two separate user interfaces for guiding data preparation persons in facilitating the transformation and creation of the data within the database. This separation allows for those parts of the data preparation process (that do not contain substantive legal information) to be processed by persons with little or no background in law, whereas those parts of the data preparation process that do contain substantive legal information can be processed by persons with greater knowledge in the legal field. This provides a more efficient and cost-effective mechanism for data to be transformed and created within the database. However, it should be understood that such a process can be structured in other ways, such as where the persons with little or no background in law can perform all party identification data processing wherever it occurs within the data preparation process.

Next, an exemplary operational scenario relating to a search for docket events will be described.

Figure 14:
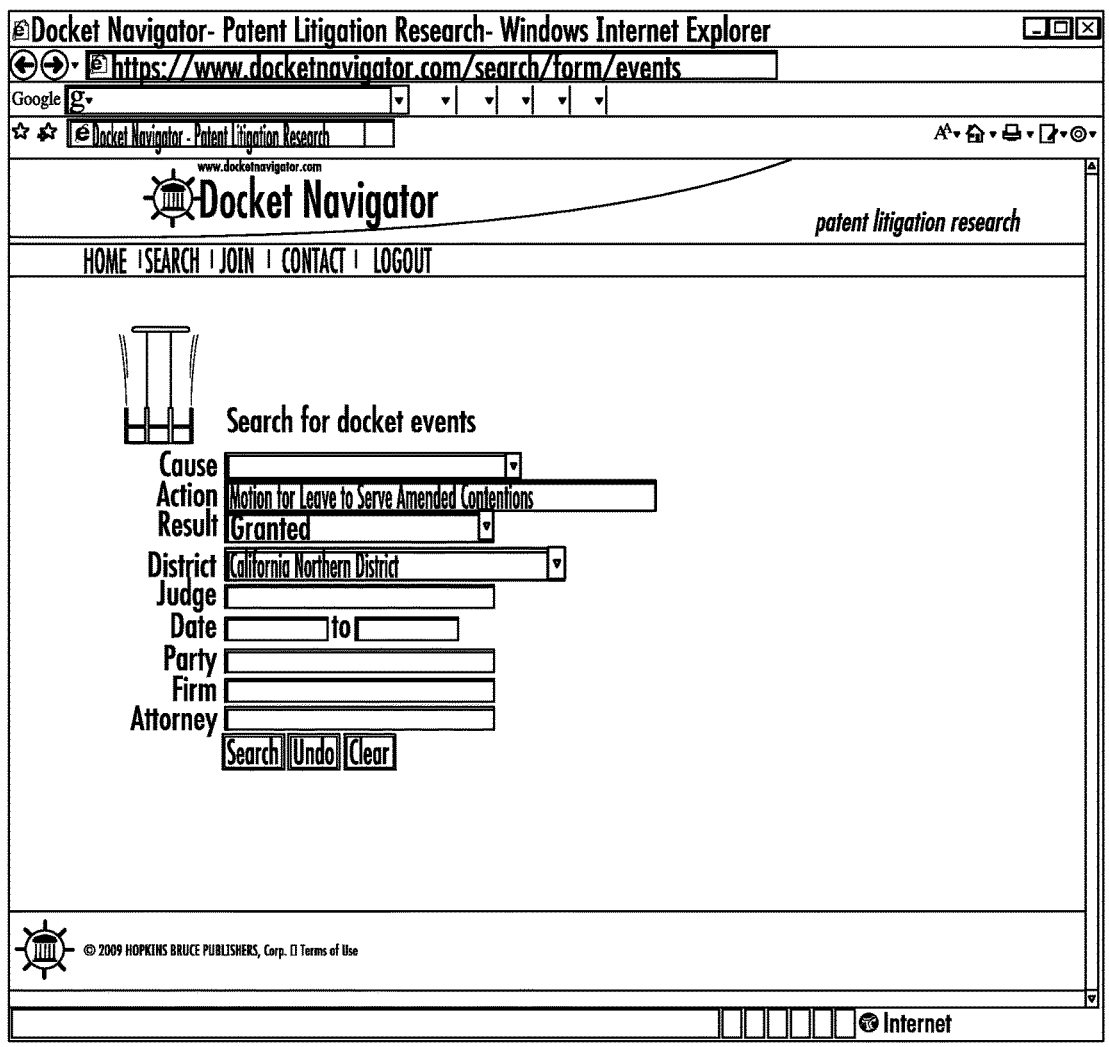
FIG. 14 is GUI input screen for querying a database for legal-related information in accordance with an aspect of the present invention.

A user can access one or more input screens for querying the database for legal-related information. For example, the screen shown in FIG. 14 allows a user to provide search information about docket events. In this operational scenario, a user has entered search values for the action field, result field, and district court field. More specifically, the user has entered in the action field a value of "Motion for Leave to Serve Amended-Contentions"; in the result field, the user has entered a value of "Granted"; and the user has entered in the district court field a value of "California Northern District."

Figure 15:
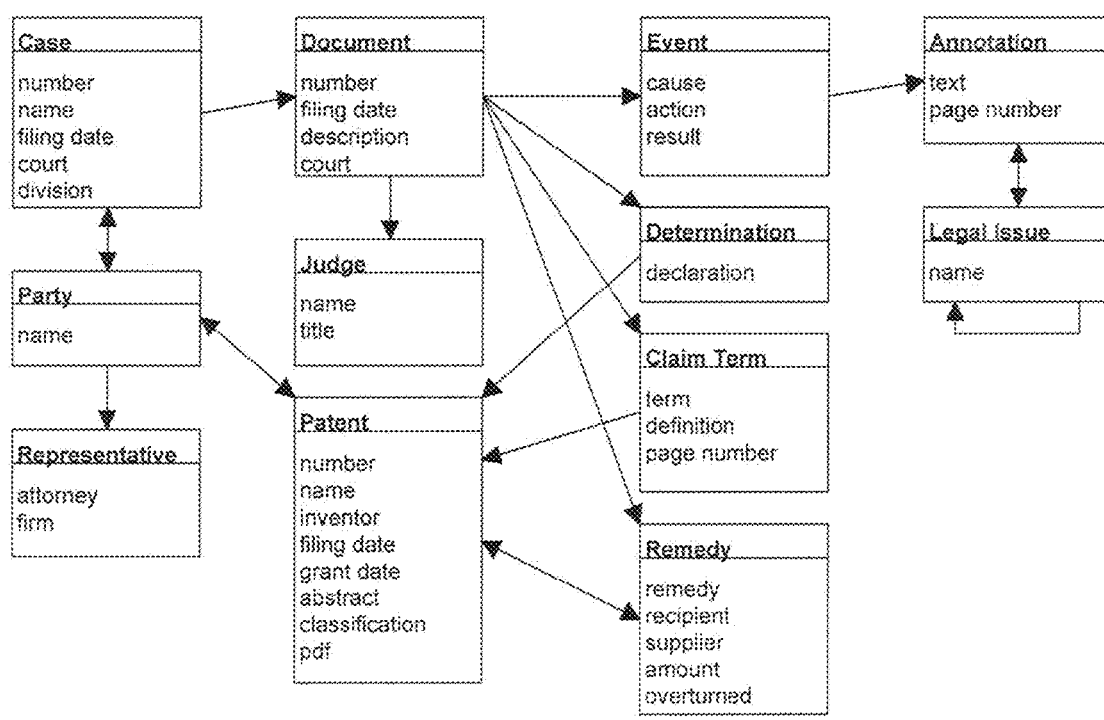
FIG. 15 is a diagram illustrating an example query formulated by the query processor in accordance with an aspect of the present invention.

After the user has clicked upon the search button, a query with the values provided in the screen is sent to the query processor. The query processor is software running in the server that formulates a query of the database, such as an SQL database statement wherein the WHERE portions of the formulated query contains the input search terms provided by the user. The query processor may also retrieve information from multiple tables in the database in order to provide comprehensive search results to the user. For example, the query processor may formulate the query based upon the example entity relationship diagram shown in FIG. 15.

Figure 16:
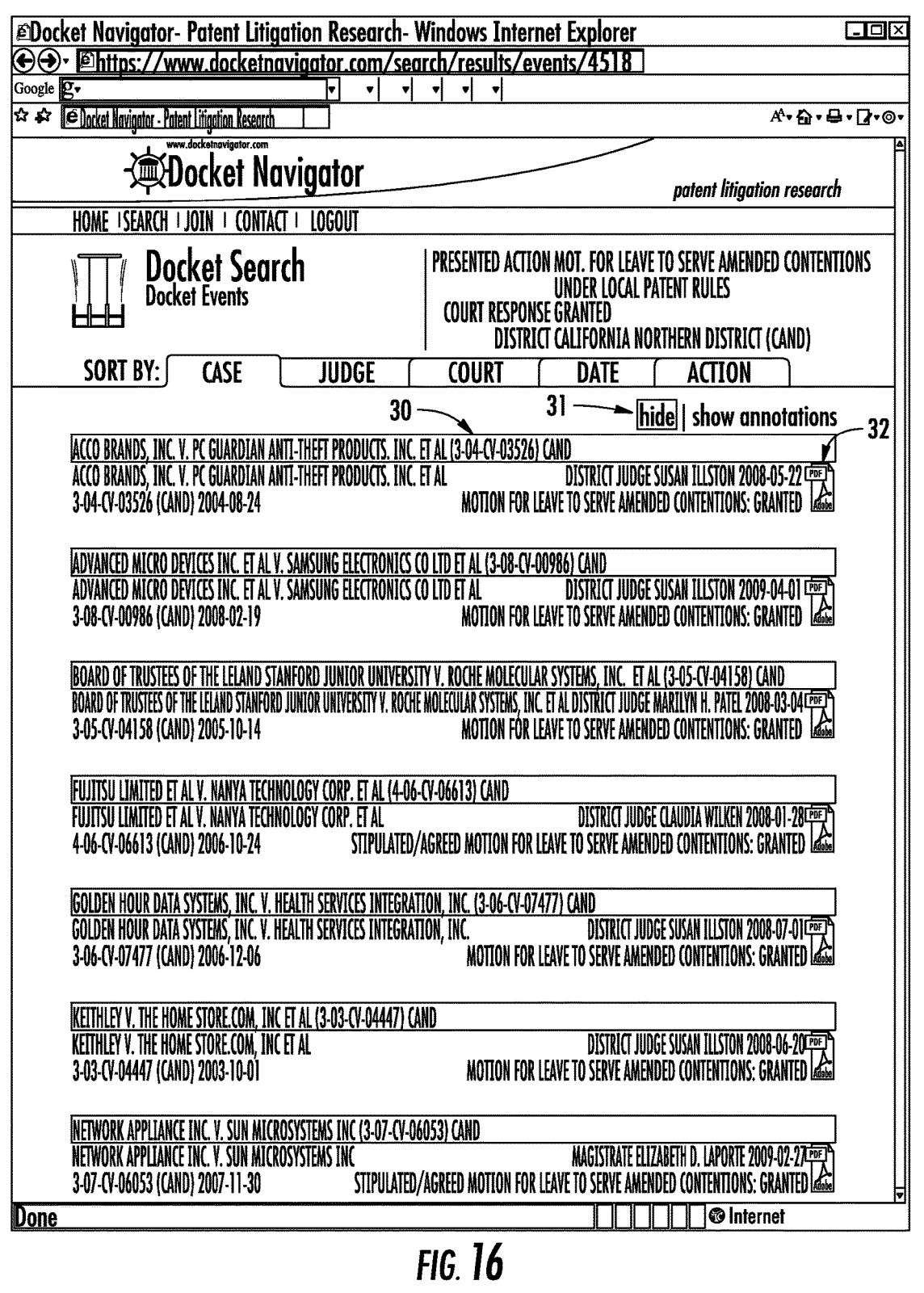

After the query has been formulated, the user is provided with the search results that satisfy the input search terms. For example, the screen shown in FIG. 16 shows an example of search results that satisfy the input search terms for the action field, result field, and district court field.

The data used to populate the screen display was obtained from the database whose schema was depicted above. For example, the title of each entry as depicted at 30 in the figure above was obtained from column name of table case. The docket number information was obtained from column number of table document. The judge-related information was obtained from columns name and title of table judge. The motion-related information was obtained from columns cause, action, and result of table event. In this operational scenario multiple tables were joined, such as the following tables: case, document, judge, event, annotation, and legal issue. The joining of the tables can be done, for example, by any relational database software, such as, for example, PostgreSQL.

It is noted that because a graphical user interface was used to assign procedural vehicle data (e.g., one or more cause, action and event for each ruling in a court's written directive), incomplete and/or inaccurate search results can be more readily avoided (as compared to searching the text of the court's written directive). For example, in United States District Courts, the Federal Rules of Civil Procedure allow the parties to seek dismissal of their opponents' claims on various grounds including, lack of subject matter jurisdiction, lack of personal jurisdiction, improper venue, insufficient process, insufficient service of process, failure to state a claim on which relief can be granted, and failure to join an indispensable party.

Although the grounds for each type of motion vary significantly, they are collectively referred to generally as "motions to dismiss." Thus, in orders ruling on a particular type of motion to dismiss, courts occasionally do not explicitly state the type of motion they are ruling on, but simply use the generic term "motion to dismiss." In such situations, a simple text search of the order would not reveal the specific type of motion to dismiss the court was ruling on. Thus, that particular order would not be included in search queries designed to identify that particular type of motion to dismiss (e.g., a query seeking documents containing the phrase "motion to dismiss"). However, assigning procedural vehicle data via a graphical user interface permits data entry personnel to determine, from the substance of the order and/or information external to the order itself, which type of motion to dismiss the court was ruling on. In such situations, a user may form a query that will identify all orders ruling on a particular type of motion to dismiss regardless of the specific words contained in such order.

As an additional example, in United States District Courts, the Federal Rules of Civil Procedure specify that motions to dismiss for failure to state a claim should be based upon the pleadings. However, if the moving party submits evidence with the motion, the court is empowered to consider the motion as one for summary judgment. In such instances, the court's order ruling on the motion is properly classified as a ruling on a motion for summary judgment and not a ruling on a motion to dismiss. Yet text searches of the order itself could falsely identify the order as one for dismissal.

With reference back to the instant operational scenario, the user can view different information as well as more detailed data than what is presented on the screen display of FIG. 16. As an illustration, preferably the functionality is provided so that the user can click upon the PDF icon, which represents a link to a PDF document. The icon representing the link is depicted as 32 in FIG. 16, and in this case is associated with a particular displayed item in order to see specific information about a motion. An example of such an item is depicted in the screen shown in FIG. 17.

Figure 18:
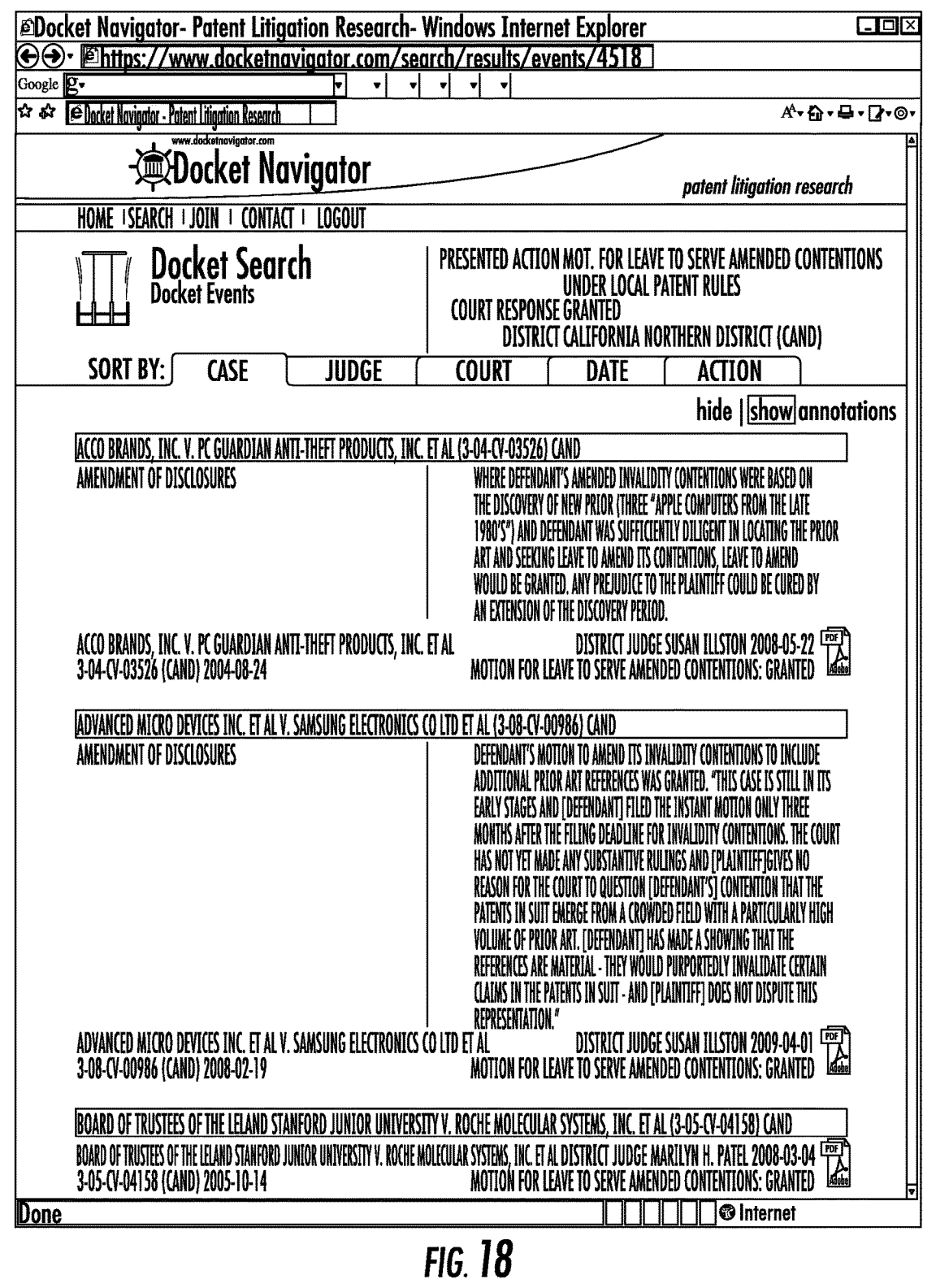

As another example, the user can click upon the "show annotations" interface item, depicted as 31 in FIG. 16, in order to reveal detailed comments about each of the displayed entries. The screen shown in FIG. 18 provides an illustration of annotations being displayed for two "amendment of disclosures."

Figure 19:
FIG. 19 is a screen shot of a GUI for permitting a user to provide search information annotations based on legal issues, docket events and other criteria.

Another operational scenario, relating to a search for annotated orders, is described below. The example begins with the screen of FIG. 19 allowing a user to provide search information annotations based on legal issues, docket events, and other criteria. In this operational scenario, a user has entered search values for the legal issues, docket event action, and docket event result. More specifically, the user has entered in the action field a value of "Motion for Summary Judgment—Patent Invalid"; in the result field, the user has entered a value of "Granted"; and the user has selected "Determining Invention/Critical Date" and "Determining Relevant Prior Art" legal issues.

After the user has clicked upon the search button, a query with the values provided in the screen is sent to the query processor. The query processor formulates a query of the database, such as an SQL database statement wherein the WHERE portions of the formulated query contains the input search terms provided by the user. The query processor may also retrieve information from multiple tables in the database in order to provide comprehensive search results to the user. After the query has been formulated, the user is provided with the search results that satisfy the input search terms.

Figure 20:
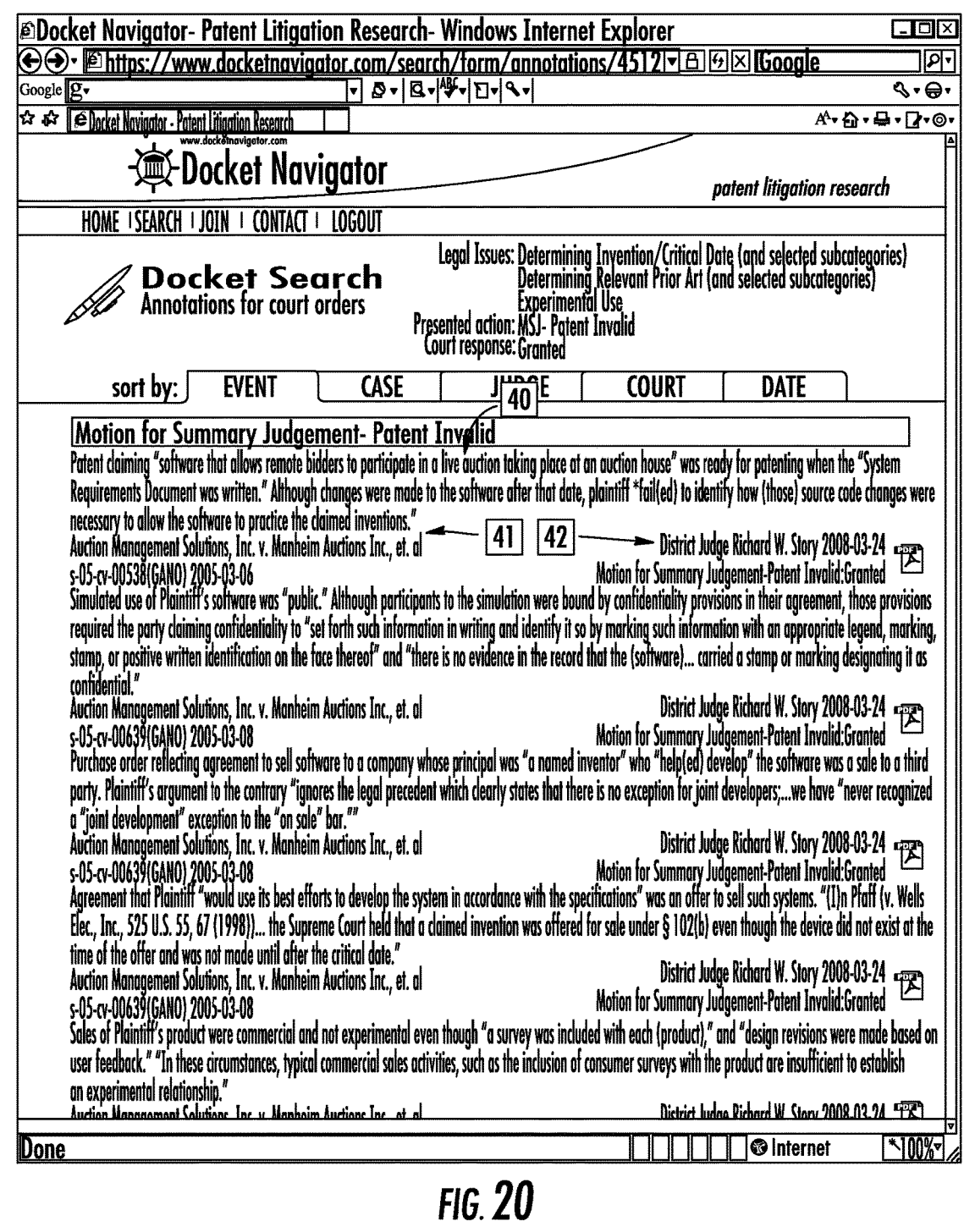

For example, the screen in FIG. 20 shows an example of search results that satisfy the input search terms for the legal issues selection, docket event action field, and docket event result field. The data used to populate the screen display was obtained from the database whose relationships were depicted above. For example, the text of each entry as depicted at 40 in FIG. 20 was obtained from column text of table annotation. The citation information of each entry as depicted at 41 and 42 in the figure above was obtained from column name and number of table case, from columns name and title of table judge, and from columns cause, action, and result of table event. In this operational scenario multiple tables were joined, such as the following tables: case, document, judge, event, annotation, and legal issue.

Preferably the GUI provides the user with tabs to allow the user to view different orderings of the information as well as more detailed data than what is presented on the above screen display. For example, the user can click upon the "court" tab interface item to see the same information arranged primarily by court. An example of this is depicted in the screen shown in FIG. 21.

Figure 22:
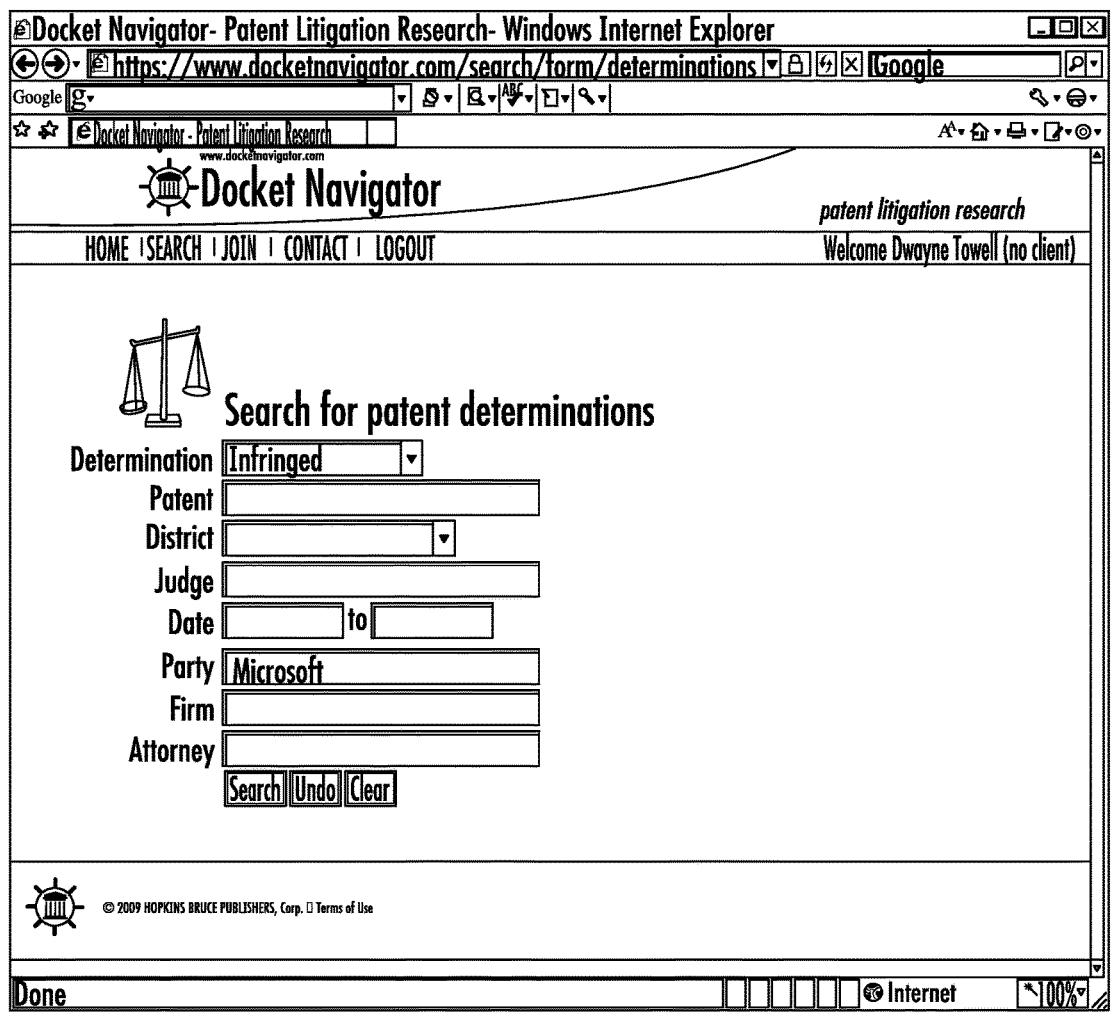
FIG. 22 is a screen shot of a GUI allowing a user to provide search information for patent determinations.

An operational scenario relating to research of a patent litigation history example will next be described. This example relates particularly to researching prior patent determinations. The screen shown in FIG. 22 allows a user to provide search information for patents determinations based on type of determination, patent, district, judge, party, and other criteria. In this operational scenario, a user has entered search values for the determination type and a party involved. More specifically, the user has entered in the determination field a value of "Infringed" and in the party field, the user has entered a value of "Microsoft".

After the user has clicked upon the search button, a query with the values provided in the screen is sent to the query processor. The query processor formulates a query of the database, such as an SQL database statement wherein the WHERE portions of the formulated query contains the input search terms provided by the user. The query processor may also retrieve information from multiple tables in the database in order to provide comprehensive search results to the user. After the query has been formulated, the user is provided with the search results that satisfy the input search terms. For example, the screen of FIG. 23 shows an example of search results that satisfy the input search terms for infringed patents involving Microsoft as a party.

The data used to populate the screen display was obtained from the database whose relationships were depicted above. For example, the text of each entry as depicted at 50 in FIG. 23 was obtained from columns name and number of table case. The judicial officer information of each entry as depicted at 51 in FIG. 23 was obtained from columns name and title of table judge as well as column filing date from table document. The patent information of each entry as depicted at 52 in FIG. 23 was obtained from columns number and inventor of table patent as well as column declaration from table determination. In this operational scenario multiple tables were joined, such as the following tables: case, document, judge, party, patent, and determination.

Figure 23:
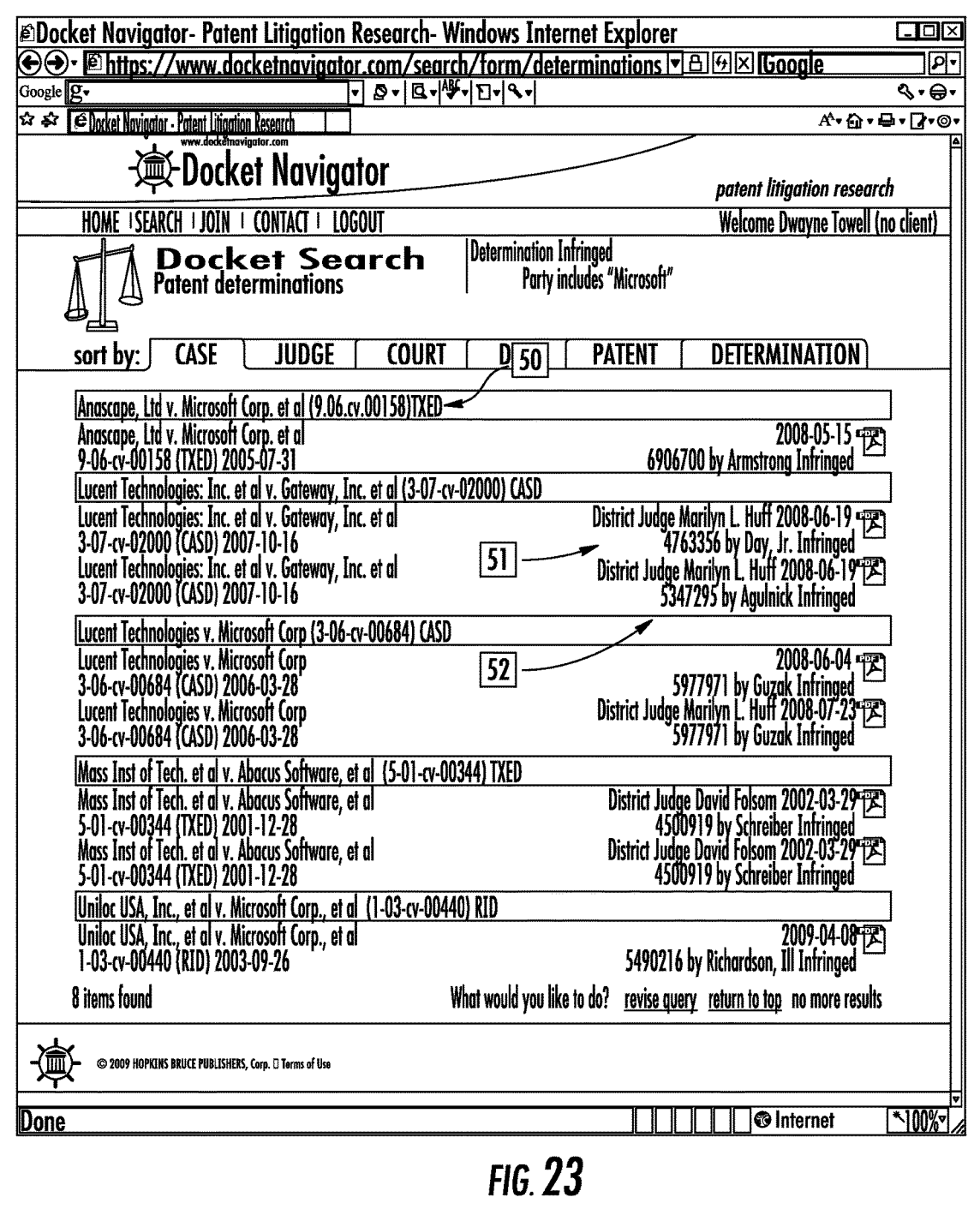

The user can view different orderings of the information as well as more detailed data than what is presented on the screen display of FIG. 23. For example, the user can click upon the "date" tab interface item to see the same information arranged primarily by date. An example of this is depicted in the screen of FIG. 24.

Almost all data items in the interface represent options to further explore detailed information about the specific item. For example, the number "U.S. Pat. No. 5,347,295", as depicted at 60 in FIG. 24, can be clicked to display detailed information about that specific patent.

An example of this is depicted in the screen shown in FIG. 25. This detailed report for U.S. Pat. No. 5,347,295 is typical of the data depicted in the database. Tab interface items allow the user to select the specific information of interest. In the example shown in FIG. 25 the "abstract" tab shows information from table patent for this specific patent. Clicking on other tabs displays information from other tables which relate to this patent.

Figure 26:
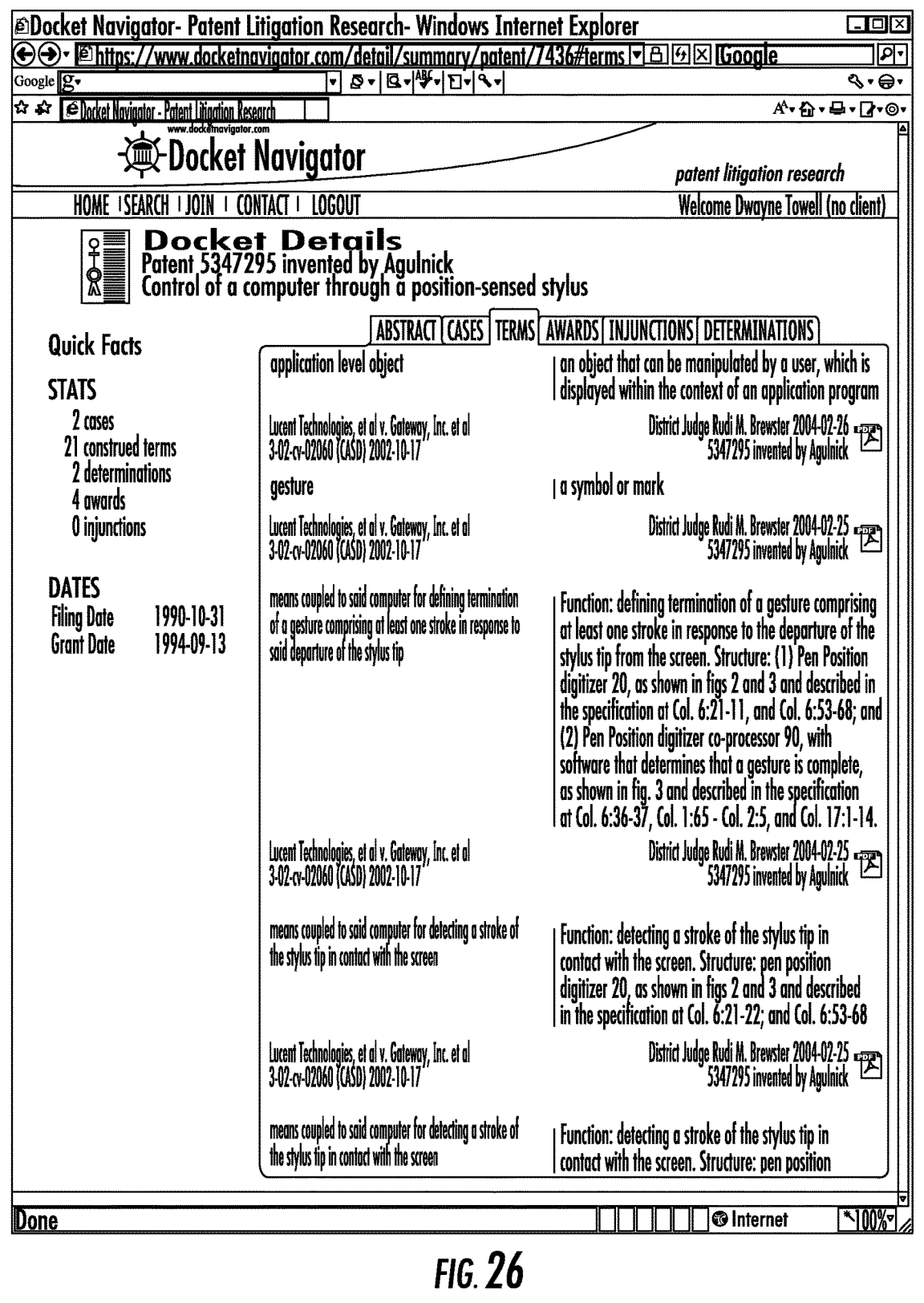
Figure 27:
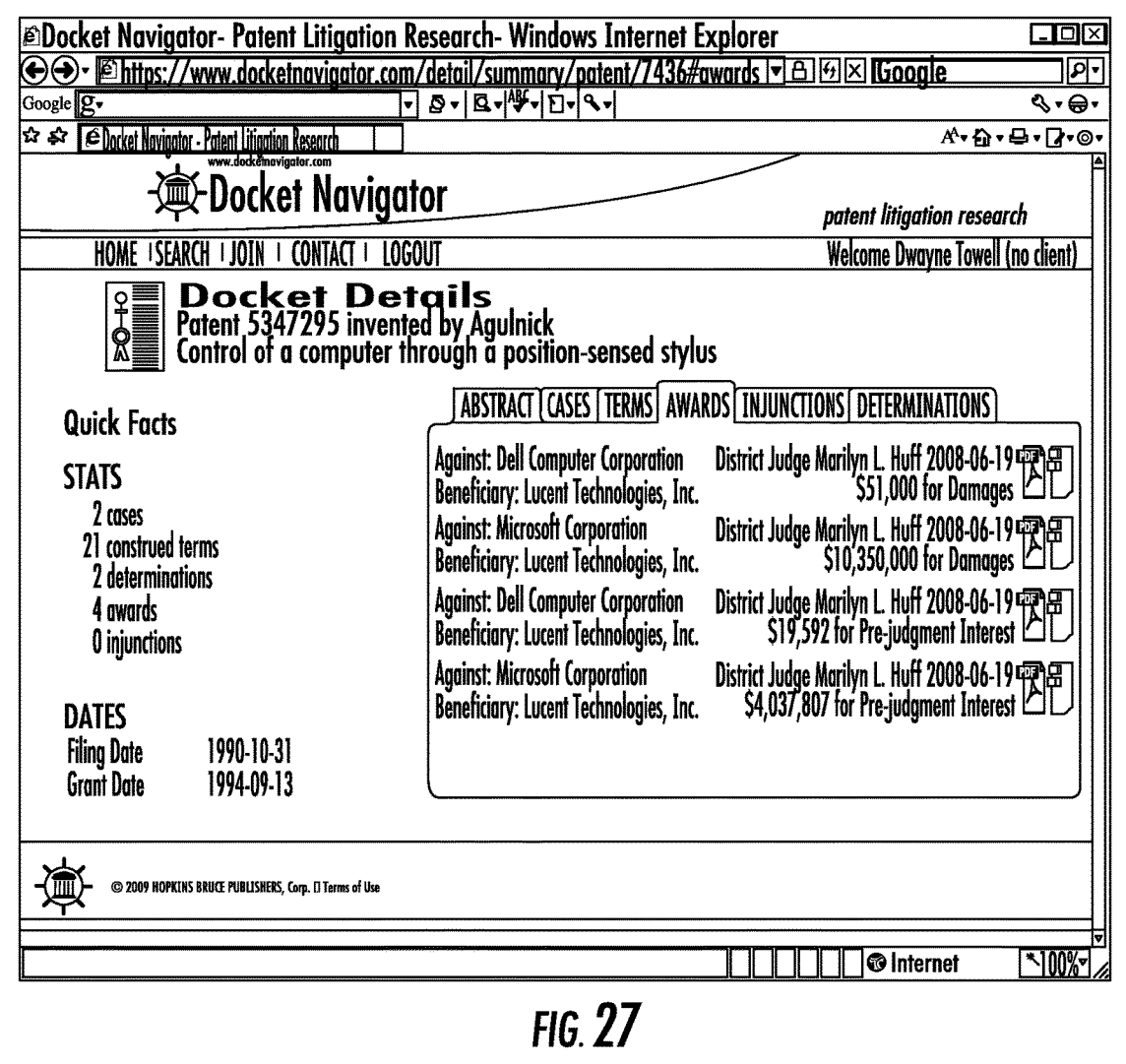
Figure 28:
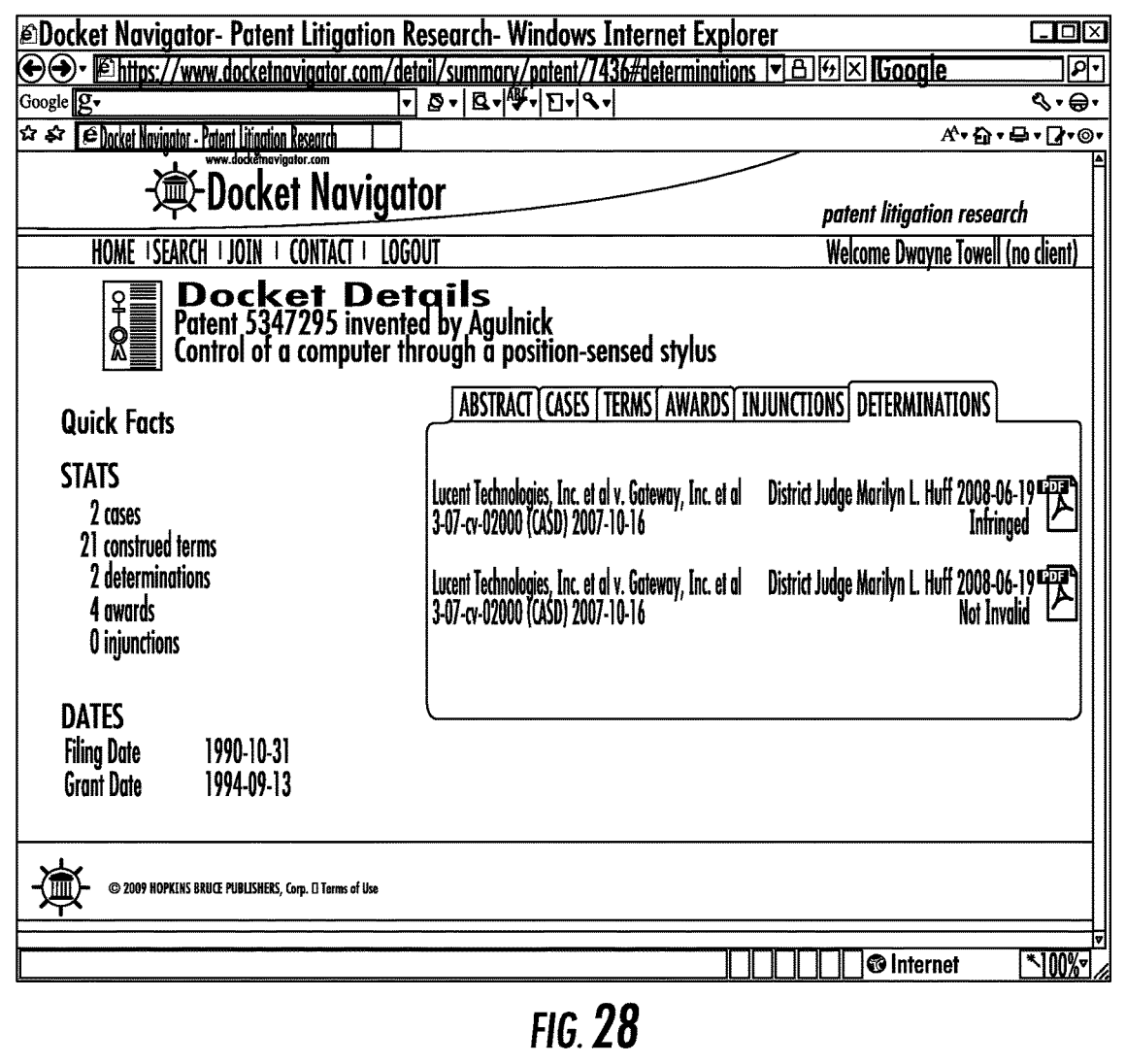

For example, selecting the "terms" tab interface item displays the information included in the figure shown in FIG. 26. Selecting the "awards" tab interface item displays the information included in the figure shown FIG. 27. Selecting the "determinations" tab interface item displays the information included in the figure shown FIG. 28.

Next will be described an operational scenario for creating a newsletter of recent court activity. In this operational scenario, the database of court activity is queried for all items which have not yet been reported via the newsletter. This is accomplished by selecting all records which have not been associated with a newsletter. A user is presented with this list of unreported data items and allowed to select specific items to be reported.

Figures 29, 29A, 29B:
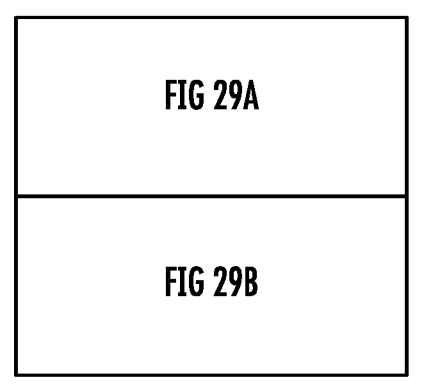
Figure 29A:
FIG. 29 is an example of a newsletter of recent court activity generated in accordance with an aspect of the present invention.

After selected items to report, a potential newsletter is generated which includes the selected items and related contextual information. For example, each new case reported includes the presiding judge, parties, representatives and patents involved. Another example involves determinations; each determination includes the case, patent involved and the court order document. If the potential newsletter is approved by the user, a final, fully-formatted version is created, a newsletter record is created, and all selected records are associated with the newly created newsletter. In a preferred embodiment, the final formatted version is created as a web page and delivered via email. An example of such a newsletter is available in FIG. 29.

While examples have been used to disclose the invention, including the best mode, and also to enable any person skilled in the art to make and use the invention, the patentable scope of the invention is defined by claims, and may include other examples that occur to those skilled in the art. Accordingly the examples disclosed herein are to be considered non-limiting. As an illustration, the systems and methods may be implemented on various types of computer architectures, such as for example in a client-server configuration or in an application service provider configuration.

It is further noted that the systems and methods may include data signals conveyed via networks (e.g., local area network, wide area network, internet, combinations thereof, etc.), fiber optic medium, carrier waves, wireless networks, etc. for communication with one or more data processing devices. The data signals can carry any or all of the data disclosed herein that is provided to or from a device.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, etc.) that contain instructions (e.g., software) for use in execution by a processor to perform the methods' operations and implement the systems described herein.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise; the phrase "exclusive or" may be used to indicate situation where only the disjunctive meaning may apply.

What is claimed is:

1. A method, on one or more servers comprising one or more computers connected to a network, of analysis and presentation of court document information, the method comprising:
   querying a source of judicial decision records for a plurality of court documents reflecting respective court rulings in a plurality of respective court cases, wherein the rulings reflect past activity of the court;
   assigning, based at least in part on input received from a user interface, for each respective court ruling associated with a court document of the plurality of court documents to one or more of pre-defined categories relating to the ruling, the one or more pre-defined categories including at least three of:
   a type of procedural vehicle that led to the ruling,
   a description of a procedural vehicle that led to the ruling, wherein the procedural vehicle comprises a species of pleading application, petition or motion presented to a judicial officer requesting a decision of the judicial officer on a request to be considered by the court,
   a patent at issue in a judicial proceeding to which the ruling is assigned, and
   the court's ruling, wherein the court's ruling comprises the decision of the judicial officer on the request to be considered by the court; and
   arranging the categorized court rulings in a searchable database, such that the court documents can be searched on the basis of at least one or more of the assigned pre-defined categories.

2. The method according to claim 1, further comprising:
   at least one of the one or more servers sending a query to a court document server requesting new or changed data since a previous such query was processed, the query being structured such that:
   (a) for a case for which a case record does not exist in the searchable database, a server creates a new case record for the case, a server retrieves docket sheet information for the case comprising one or more of: (i) electronic copies of court documents filed in the case, (ii) docket entries, (iii) party information, (iv) attorney information, and (v) law firm information, and a server adds the docket sheet information to the new case record in the searchable database; and
   (b) for a case for which a case record exists in the searchable database, a server retrieves a case record for the case, a server updates the docket sheet information for the case, and a server adds the updated docket sheet information to the case record in the searchable database.

3. The method according to claim 1, further comprising, in response to receipt of a query to the searchable database, at least one of the one or more servers providing a viewable search result arranged in relation to the at least one pre-defined category.

4. The method according to claim 1, wherein the user interface is a graphical user interface.

5. The method according to claim 1, wherein at least one of the one or more servers arranges the categorized court rulings in the searchable database, such that the court documents can be searched on the basis of one or more categories of docket sheet information comprising one or more of: (i) electronic copies of the court documents, (ii) docket entries, (iii) party information, (iv) attorney information, and (v) law firm information.

6. The method according to claim 1, wherein the searchable database is searchable on the basis of at least one or more of the assigned pre-defined categories and one or more categories of docket sheet information comprising one or more of: (i) electronic copies of the court documents, (ii) docket entries, (iii) party information, (iv) attorney information, and (v) law firm information.

7. The method according to claim 1, further comprising at least one of the one or more servers generating and distributing an electronic newsletter, the newsletter comprising at least one or more of the predefined categories relating to at least one case.

8. The method according to claim 1, wherein the one or more pre-defined categories includes at least two of:
   (a) a type of procedural vehicle that led to the ruling;
   (b) a description of the procedural vehicle that led to the ruling; and
   (c) the court's ruling.

9. The method according to claim 1, wherein the one or more pre-defined categories includes at least:
   (a) a type of procedural vehicle that led to the ruling;
   (b) a description of the procedural vehicle that led to the ruling; and
   (c) the court's ruling.

10. The method according to claim 1, wherein the one or more pre-defined categories includes:
   (a) a type of procedural vehicle that led to the ruling; and
   at least one of:
   (b) a description of the procedural vehicle that led to the ruling; and
   (c) the court's ruling.

11. A court document analysis and presentation system, the system comprising:
one or more servers comprising one or more computers connected to a network, the one or more servers being configured to:
query a source of judicial records for a plurality of court documents reflecting respective court rulings in a plurality of respective court cases, wherein the rulings reflect past activity of the court;
assign, based at least in part on input received from a user interface, for each respective court ruling associated with a court document of the plurality of court documents to one or more of predefined categories relating to the ruling, the one or more pre-defined categories including at least three of:
a type of procedural vehicle that led to the ruling, wherein the procedural vehicle comprises a species of pleading application, petition or motion presented to a judicial officer requesting a decision of the judicial officer on a request to be considered by the court,
a patent at issue in a judicial proceeding to which the ruling is assigned,
a description of a procedural vehicle that led to the ruling; and
the court's ruling, wherein the court's ruling comprises the decision of the judicial officer on the request to be considered by the court; and
arrange the categorized court rulings in a searchable database, such that the court documents can be searched on the basis of at least one or more of the assigned pre-defined categories.

12. The system according to claim 11, the one or more servers being configured to:
send a query to a court document server requesting new or changed data since a previous such query was processed, the query being structured such that:
(a) for a case for which a case record does not exist in the searchable database, a server creates a new case record for the case, a server retrieves docket sheet information for the case comprising one or more of: (i) electronic copies of court documents filed in the case, (ii) docket entries, (iii) party information, (iv) attorney information, and (v) law firm information, and a server adds the docket sheet information to the new case record in the searchable database; and
(b) for a case for which a case record exists in the searchable database, a server retrieves a case record for the case, a server updates the docket sheet information for the case, and a server adds the updated docket sheet information to the case record in the searchable database.

13. The system according to claim 11, the one or more servers being further configured to, in response to receipt of a query to the searchable database, provide a viewable search result arranged in relation to the at least one pre-defined category.

14. The system according to claim 11, wherein the user interface is a graphical user interface.

15. The system according to claim 11, wherein the one or more servers are configured to arrange the categorized court rulings in the searchable database, such that the court documents can be searched on the basis of one or more categories of docket sheet information comprising one or more of: (i) electronic copies of the court documents, (ii) docket entries, (iii) party information, (iv) attorney information, and (v) law firm information.

16. The system according to claim 11, wherein the searchable database is searchable on the basis of at least one or more of the assigned pre-defined categories and one or more categories of docket sheet information comprising one or more of: (i) electronic copies of the court documents, (ii) docket entries, (iii) party information, (iv) attorney information, and (v) law firm information.

17. The system according to claim 11, the one or more servers being configured to generate and distribute an electronic newsletter, the newsletter comprising at least one or more of the predefined categories relating to at least one case.

18. The system according to claim 11, wherein the one or more pre-defined categories includes at least two of:
(a) a type of procedural vehicle that led to the ruling;
(b) a description of the procedural vehicle that led to the ruling; and
(c) the court's ruling.

19. The system according to claim 11, wherein the one or more pre-defined categories includes at least:
(a) a type of procedural vehicle that led to the ruling;
(b) a description of the procedural vehicle that led to the ruling; and
(c) the court's ruling.

20. The system according to claim 11, wherein the one or more pre-defined categories includes:
(a) a type of procedural vehicle that led to the ruling; and at least one of:
(b) a description of the procedural vehicle that led to the ruling; and
(c) the court's ruling.

21. A non-transitory computer-readable storage medium storing a program that, when run by one or more servers comprising one or more computers connected to a network, causes the one or more servers to perform the following steps:
querying a source of judicial records for a plurality of court documents reflecting respective court rulings in a plurality of respective court cases, wherein the rulings reflect past activity of the court;
assigning, based at least in part on input received from a user interface, for each respective court ruling associated with a court document of the plurality of court documents to one or more of pre-defined categories relating to the ruling, the one or more pre-defined categories including at least three of:
a type of procedural vehicle that led to the ruling,
a description of a procedural vehicle that led to the ruling, wherein the procedural vehicle comprises a species of pleading application, petition or motion presented to a judicial officer requesting a decision of the judicial officer on a request to be considered by the court,
a patent at issue in a judicial proceeding to which the ruling is assigned, and
the court's ruling, wherein the court's ruling comprises the decision of the judicial officer on the request to be considered by the court; and
arranging the categorized court rulings in the searchable database, such that the court documents can be searched on the basis of at least one or more of the assigned pre-defined categories.

22. The computer-readable medium according to claim 21, the steps further comprising:
sending a query to a court document server requesting new or changed data since a previous such query was processed, the query being structured such that:

(a) for a case for which a case record does not exist in the searchable database, a server creates a new case record for the case, a server retrieves docket sheet information for the case comprising one or more of: (i) electronic copies of court documents filed in the case, (ii) docket entries, (iii) party information, (iv) attorney information, and (v) law firm information, and a server adds the docket sheet information to the new case record in the searchable database; and (b) for a case for which a case record exists in the searchable database, a server retrieves a case record for the case, a server updates the docket sheet information for the case, and a server adds the updated docket sheet information to the case record in the searchable database.

23. The computer-readable medium according to claim 21, the steps further comprising, in response to receipt of a query to the searchable database, providing a viewable search result arranged in relation to the at least one pre-defined category.

24. The computer-readable medium according to claim 21, wherein the user interface is a graphical user interface.

25. The computer-readable medium according to claim 21, wherein the searchable database is searchable on the basis of at least one or more of the assigned pre-defined categories and one or more categories of docket sheet information comprising one or more of (i) electronic copies of the court documents, (ii) docket entries, (iii) party information, (iv) attorney information, and (v) law firm information.

26. The computer-readable medium according to claim 21, the steps further comprising generating and distributing an electronic newsletter, the newsletter comprising at least one or more of the predefined categories relating to at least one case.

27. The computer-readable medium according to claim 21, wherein the one or more pre-defined categories includes at least two of:
    (a) a type of procedural vehicle that led to the ruling;
    (b) a description of the procedural vehicle that led to the ruling; and
    (c) the court's ruling.

28. The computer-readable medium according to claim 21, wherein the one or more pre-defined categories includes at least:
    (a) a type of procedural vehicle that led to the ruling;
    (b) a description of the procedural vehicle that led to the ruling; and
    (c) the court's ruling.

29. The computer-readable medium according to claim 21, wherein the one or more pre-defined categories includes:
    (a) a type of procedural vehicle that led to the ruling; and at least one of:
    (b) a description of the procedural vehicle that led to the ruling; and
    (c) the court's ruling.

30. The computer-readable medium according to claim 21, wherein the querying comprises querying, over a computer network, a remote server including the source of judicial decision records for the plurality of court documents reflecting the respective court rulings in the plurality of respective court cases.

* * * * *